(12) United States Patent
Cho et al.

(10) Patent No.: US 10,988,757 B2
(45) Date of Patent: Apr. 27, 2021

(54) MAGNETIC NANOSTRUCTURE FOR DETECTING AND ISOLATING CELL-FREE DNA COMPRISING CATIONIC POLYMER AND MAGNETIC-NANOPARTICLE-CONTAINING CONDUCTIVE POLYMER

(71) Applicant: GENOPSY CO., LTD., Seoul (KR)

(72) Inventors: Youngnam Cho, Goyang-si (KR); Eun Sook Lee, Goyang-si (KR); HyungJae Lee, Seoul (KR); Ji-Youn Han, Goyang-si (KR); Sang-Hyun Hwang, Seoul (KR)

(73) Assignee: GENOPSY CO., LTD., Seoul (KR)

( * ) Notice: Subject to any disclaimer, the term of this patent is extended or adjusted under 35 U.S.C. 154(b) by 16 days.

(21) Appl. No.: 15/478,792

(22) Filed: Apr. 4, 2017

(65) Prior Publication Data

US 2018/0179515 A1 Jun. 28, 2018

(30) Foreign Application Priority Data

Dec. 23, 2016 (KR) .......................... 10-2016-0177867

(51) Int. Cl.
  *C12N 15/10* (2006.01)
  *C12Q 1/68* (2018.01)
  (Continued)

(52) U.S. Cl.
  CPC ....... *C12N 15/1013* (2013.01); *C12Q 1/6806* (2013.01); *C12Q 1/6886* (2013.01); *C12Q 2600/156* (2013.01)

(58) Field of Classification Search
  None
  See application file for complete search history.

(56) References Cited

U.S. PATENT DOCUMENTS

| | | | |
|---|---|---|---|
| 8,768,451 B2* | 7/2014 | Atanasoska | A61N 1/20 604/20 |
| 2004/0132070 A1* | 7/2004 | Star | G01N 33/566 435/6.19 |

(Continued)

FOREIGN PATENT DOCUMENTS

| | | |
|---|---|---|
| KR | 10-2016-0129523 A | 11/2016 |
| WO | 2010/005444 A1 | 1/2010 |

OTHER PUBLICATIONS

Arakaki et al., Formation of magnetite by bacteria and its application. J. R. Soc. Interface (2008) 5, 977-999. (Year: 2008).*

(Continued)

*Primary Examiner* — Arthur S Leonard
(74) *Attorney, Agent, or Firm* — Vorys, Sater, Seymour & Pease LLP; Mih Suhn Koh

(57) ABSTRACT

Provided is a magnetic nanostructure for detecting and isolating cell-free DNA (cfDNA) that including a cationic polymer and a magnetic-nanoparticle-containing conductive polymer. The magnetic nanostructure for detecting and isolating cfDNA according to the subject matter can significantly improve detection and extraction efficiencies of DNA present in a urine, CSF, blood plasma, or blood sample, and exhibits an enhanced sensitivity. Therefore, it is expected that the magnetic nanostructure for detecting and isolating cfDNA according to the subject matter will be used for extracting DNA for use in a genetic mutation diagnosis service as well as for an early cancer diagnosis and cancer treatment.

7 Claims, 34 Drawing Sheets

(51) Int. Cl.
  *C12Q 1/6886* (2018.01)
  *C12Q 1/6806* (2018.01)

(56) References Cited

U.S. PATENT DOCUMENTS

| | | | | |
|---|---|---|---|---|
| 2004/0168916 | A1* | 9/2004 | Fuchs | C12M 47/04 |
| | | | | 204/451 |
| 2011/0171137 | A1* | 7/2011 | Patolsky | B82Y 15/00 |
| | | | | 424/9.3 |
| 2012/0083037 | A1* | 4/2012 | Wendorff | A61K 48/0041 |
| | | | | 435/455 |
| 2014/0356411 | A1* | 12/2014 | Fan | G01N 21/658 |
| | | | | 424/443 |
| 2015/0132758 | A1* | 5/2015 | Medina-Llamas | |
| | | | | C12N 15/1013 |
| | | | | 435/6.11 |
| 2015/0307870 | A1* | 10/2015 | Fabis | C01G 49/06 |
| | | | | 536/25.4 |
| 2015/0345048 | A1* | 12/2015 | Tokarev | D01D 5/00 |
| | | | | 264/429 |

OTHER PUBLICATIONS

Gai et al., Surfactant-free synthesis of Fe3O4@PANI and Fe3O4@PPy microspheres as adsorbents for isolation of PCR-ready DNA. Dalton Trans., 2013, 42, 1820 (Year: 2013).*

Castro-Smirnov et al., Physical interactions between DNA and sepiolite nanofibers, and potential application for DNA transfer into mammalian cells. Sci Reports, 2016, 6:36341, p. 1-14 (Year: 2016).*

Miodek et al., Electrochemicalfunctionalizationofpolypyrrolethrou ghamine oxidationofpoly(amidoamine)dendrimers:Application toDNA biosensor. Talanta154(2016)446-454 (Year: 2016).*

Hong et al. An integrated multifunctional platform based on biotin-doped conducting polymer nanowires for cell capture, release, and electrochemical sensing. Biomaterials, 2014, 35:9573-9580 (Year: 2014).*

Lee et al., "Magnetic nanowires for rapid and ultrasensitive isolation of DNA from cervical specimens for the detection of multiple human papillomaviruses genotypes" Biosensors and Bioelectronics, vol. 86, pp. 864-870, Jul. 20, 2016, x.

Chiang et al., "Application of superparamagnetic nanoparticles in purification of plasmid DNA from bacterial cells", Journal of Chromatography B, vol. 822, pp. 54-60, (2005).

Hong et al., "Multifunctional magnetic nanowires: A novel breakthrough for ultrasensitive detection and isolation of rare cancer cells from non-metastatic early breast cancer patients using small volumes of blood", Biomaterials, vol. 106, pp. 78-85, (2016).

Jeon et al., "Efficient Capture and Isolation of Tumor-Related Circulating Cell-Free DNA from Cancer Patients Using Electroactive Conducting Polymer Nanowire Platforms", Theranostics, vol. 6, Issue 6, pp. 828-836, (2016).

Luo et al., "Enhanced magnetic performance of metal-organic nanowire arrays by FeCo/polypyrrole co-electrodeposition", Journal of Applied Physics, vol. 113, pp. 17B908-1-17B908-3, (2013).

Okawa et al., "Cell Rupture and Nucleic Acid Extraction by Magnetic Nanowires", Japan Society of Chemistry No. 95 spring annual meeting proceedings vol. II, 2 B4-33, p. 200, (2015).

Pan et al., "Stimulation of Gene Transfection by Silicon Nanowire Arrays Modified with Polyethylenimine", ACS Appl. Mater. Interfaces, vol. 6, pp. 14391-14398, (2014).

* cited by examiner

FIG. 4A

|  | No. positive/ No. tested | Mean $C_T$ | Positive (%) |
|---|---|---|---|
| SiHa (HPV16) (cells/ml) | | | |
| 50 | 10/10 | 34.3 | 100 |
| 30 | 10/10 | 35.9 | 100 |
| 10 | 10/10 | 37.4 | 100 |
| 3 | 1/10 | - | 10 |
| HeLa (HPV18) (cells/ml) | | | |
| 50 | 10/10 | 35.2 | 100 |
| 30 | 10/10 | 36.3 | 100 |
| 10 | 10/10 | 37.3 | 100 |
| 3 | 8/10 | 38.7 | 80 |

FIG. 5A

| Patient sample | PEI-MNW | | | Cobas | | | ΔCt |
|---|---|---|---|---|---|---|---|
| | HPV16 | HPV18 | 12 other types | HPV16 | HPV18 | 12 other types | |
| P1 | 22.5 | | | 25.6 | | | 3.1 |
| P2 | 21.4 | | | 23.0 | | | 1.6 |
| P3 | 32.6 | | | 33.1 | | | 0.5 |
| P4 | 26.2 | | | 30.9 | | | 4.7 |
| P5 | 26.2 | | | 29.4 | | | 3.2 |
| P6 | 26.6 | | | 29.3 | | | 2.7 |
| P7 | 24.8 | | | 26.2 | | | 1.4 |
| P8 | 32.9 | | | 34.1 | | | 1.2 |
| P9 | 25.7 | | | 28.7 | | | 3.0 |
| P10 | 25.8 | | | 26.2 | | | 0.4 |
| P11 | 31.7 | | | 31.9 | | | 0.2 |
| P12 | | 29.3 | | | 29.3 | | 0 |
| P13 | | 26.7 | | | 26.8 | | 0.1 |
| P14 | | | 20.2 | | | 20.5 | 0.3 |
| P15 | | | 24.9 | | | 25.6 | 0.7 |
| P16 | | 28.1 | 25.5 | | 36.6 | 27.7 | 8.5/2.2 |
| P17 | | 32.0 | 24.0 | | 32.9 | 32.2 | 0.9/8.2 |
| P18 | | | 21.0 | | | 21.2 | 0.2 |
| P19 | | | 27.0 | | | 27.6 | 0.6 |
| P20 | | | 26.8 | | | 29.8 | 3.0 |

FIG. 8

|  | No. positive/ No. tested | Mean Ct | Positive (%) |
|---|---|---|---|
| SiHa (HPV16) (cells/mL) |  |  |  |
| 100 | 10/10 | 37.0 | 100 |
| 50 | 10/10 | 37.4 | 100 |
| 30 | 10/10 | 38.4 | 100 |
| 10 | 10/10 | 38.9 | 100 |
| 3 | 0/10 | - | 0 |
| HeLa (HPV18) (cells/mL) |  |  |  |
| 100 | 10/10 | 35.8 | 100 |
| 50 | 10/10 | 36.3 | 100 |
| 30 | 10/10 | 38.0 | 100 |
| 10 | 3/10 | 39.0 | 30 |
| 3 | 2/10 | 39.0 | 20 |

FIG. 9B

| Patient sample | PEI/mPpy NWs | | | Qiagen Kit | | | ΔCt |
|---|---|---|---|---|---|---|---|
| | HPV16 | HPV18 | 12 other types | HPV16 | HPV18 | 12 other types | |
| 1 | 37.2 | | | 40.0 | | | 2.8 |
| 2 | | | 35.4 | | | 33.4 | (-2.0) |
| 3 | | | 36.0 | | | N/A | |
| 4 | 37.2 | | | | | N/A | |
| 5 | | N/A | | | 38.8 | | |
| 6 | | | 29.6 | | | 33.9 | 4.3 |
| 7 | 34.4 | | | N/A | | | |
| 8 | | | 32.8 | | | 36.8 | 4.0 |
| 9 | | | 32.7 | | | 35.2 | 2.5 |
| 10 | | | 37.2 | | | N/A | |
| 11 | | | N/A | | | 36.3 | |
| 12 | | | 34.6 | | | 40.0 | 5.4 |
| 13 | | | 28.2 | | | 29.7 | 1.5 |
| 14 | 33.9 | | | N/A | | | |
| 15 | | | 34.9 | | | 39.5 | 4.6 |
| 16 | | | 33.0 | | | 40.0 | 7.0 |
| 17 | | 31.6 | | | N/A | | |
| 18 | | | 33.7 | | | 37.8 | 4.1 |
| 19 | | | 30.7 | | | N/A | |
| 20 | | | 31.0 | | | 40.0 | 9.0 |
| 21 | 33.4 | | | 38.3 | | | 4.9 |
| 22 | | | 34.0 | | | 35.2 | 1.2 |
| 23 | 38.2 | | | N/A | | | |
| 24 | 38.0 | | | N/A | | | |
| 25 | | | 32.3 | | | 34.2 | 1.9 |
| 26 | | | 36.5 | | | N/A | |
| 27 | 34.2 | | | N/A | | | |

FIG. 10C

|  | Cervical swab | | |
|---|---|---|---|
|  | HPV positive | HPV negative | Sum |
| Urine | | | |
| HPV positive | 25 | 0 | 25 |
| HPV negative | 5 | 5 | 10 |
| Sum | 30 | 5 | 35 |

FIG. 11F

| Sample | TNM staging | Primary tumor EGFR direct sequencing | mPpy NWs Positive_Mutant | Positive_WildType | Positive_Mutant | Positive_WildType | Qiagen kit Positive_Mutant | | Positive_Mutant | Positive_WildType |
|---|---|---|---|---|---|---|---|---|---|---|
| NSCLC-1 | T3N3M1b | L858R | 27 | 1.1 | 14 | 652 | 45 | 0.067 | 652 |
| NSCLC-2 | T4N2M1a | L858R | 38 | 4.7 | 7 | 128 | 200 | 1.75 | 128 |
| NSCLC-3 | T4N2M1b | L858R | 13 | 3.3 | 4 | 111 | 8 | 0.08 | 111 |
| NSCLC-4 | T4N2M1b | L858R | 17 | 0.48 | 38 | 451 | 142 | 0.33 | 451 |
| NSCLC-5 | T4N3M1b | L858R | 60 | 1.6 | 4 | 57 | 72 | 1.28 | 57 |
| NSCLC-6 | T4N2M1a | Ex19_A750del | 10 | 1.6 | 12 | 12 | 0 | N/A | 12 |
| NSCLC-7 | T4N3M1b | Ex19_A750del | 0 | N/A | 4 | 222 | 0 | N/A | 222 |
| NSCLC-8 | T1N3M1b | Ex19_A750del | 1 | 0.5 | 2 | 134 | 0 | N/A | 134 |
| NSCLC-9 | T2N3M0 | Ex19_A750del | 20 | 1.7 | 2 | 30 | 0 | N/A | 30 |
| NSCLC-10 | T4N2M0 | Ex19_A750del | 5 | 0.7 | 7 | 150 | 0 | N/A | 150 |

1 mL blood plasma (Qiagen kit Positive_WildType column)
300 μL blood plasma (Qiagen kit Positive_Mutant column)
300 μL blood plasma (mPpy NWs columns)

FIG. 11I

| Patient No. | TNM staging | Stage | Mutation (Tissue) | Mutation (cfDNA) / 300 uL plasma |
|---|---|---|---|---|
| 1 (Blood) | T3N3M0 | IIIB | EGFR Exon 21 L858R | EGFR Exon 21 L858R |
| 2 (Blood) | | | EGFR Exon 21 L858R | EGFR Exon 21 L858R |
| 3 (Blood) | | | EGFR Exon 21 L858R | EGFR Exon 21 L858R |
| 4 (Blood) | T4N3M1b | IV | EGFR Exon 21 L858R | EGFR Exon 21 L858R |
| 5 (Blood) | T2N3M1b | IV | EGFR Exon 21 L858R | EGFR Exon 21 L858R |
| 6 (Blood) | T3N0M1b | IV | EGFR Exon 19del | EGFR Exon 19del |
| 7 (CSF) | | | EGFR Exon 19del / EGFR Exon 20 T790M | EGFR Exon 19del |
| 8 (Blood) | TXNXM1b | IV | EGFR Exon 21 L858R | EGFR Exon 21 L858R |
| 9 (Blood) | T1bN2M1b | IV | EGFR Exon 21 L858R | EGFR Exon 21 L858R |

MAGNETIC NANOSTRUCTURE FOR DETECTING AND ISOLATING CELL-FREE DNA COMPRISING CATIONIC POLYMER AND MAGNETIC-NANOPARTICLE-CONTAINING CONDUCTIVE POLYMER

The present invention was undertaken with the support of No. 1510070, No. 1611170, and No. 1611780 grant funded by a National Cancer Center, from the Ministry of Health and Welfare, the Republic of Korea.

CROSS-REFERENCE TO RELATED APPLICATION

This application claims priority to and the benefit of Korean Patent Application No. 10-2016-0177867, filed on Dec. 23, 2016, the disclosure of which is incorporated herein by reference in its entirety.

BACKGROUND

1. Field of the Invention

The present invention relates to a magnetic nanostructure for detecting and isolating cell-free DNA that includes a cationic polymer and a magnetic-nanoparticle-containing conductive polymer.

2. Discussion of Related Art

In recent years, the importance of an early cancer diagnosis has been greatly emphasized worldwide, leading to an increase in the proportion of research on methods for an early cancer diagnosis. However, until now, cancer diagnosis methods are mainly based on invasive methods such as collecting tissue samples and performing endoscopy. In particular, biopsies, which are currently the most commonly used methods, are carried out by removing a part of an area suspicious of being diseased and examining the same under a microscope, and thus require cutting a human body using a needle, punch, endoscope, laparoscope, or the like for tissue sample collection, resulting in considerable patient discomfort, a scar, and a long patient recovery time.

As an alternative to existing invasive diagnosis and testing methods, molecular diagnostics based on liquid biosensors is drawing attention. Being a non-invasive method, a liquid biopsy quickly produces test results, and, unlike biopsy tissue samples from which a disease can be only partly analyzed, liquid biopsy samples (i.e., body fluid) can be used for a multilateral analysis of a disease. In particular, liquid biopsies are expected to be highly useful for a cancer diagnosis and capable of the detailed examination of cancer development, metastasis, and the like through an analysis of cancer cell-derived DNA present in the blood of various body parts only by analyzing body fluid such as blood and urine.

Also, molecular diagnostics, which is a representative in-vitro diagnosis technique, is a diagnosis technique that involves detecting, based on numerical results or images, molecular-level changes in DNA and RNA in a sample (e.g., blood or urine) containing genetic information. Since molecular diagnostics is highly accurate and does not require a biopsy, efforts are being made to apply molecular diagnostics to cancer diagnosis techniques by taking advantage of rapidly developing genome analysis technology and in pursuit of cost reduction.

Also, cell-free DNA (cfDNA) refers to cancer cell-derived DNA that is derived from a tumor cell and can be found in a biological sample (e.g., blood, blood plasma, or urine) obtained from a cancer patient. After necrosis or cell death, or by being activated in a normal cell and/or cancer cell of a urinary tract, such cfDNA is released through urine, blood, or the like via various cell physiological processes. Therefore, as techniques of isolating and detecting cfDNA derived from a biological sample (e.g., blood, blood plasma, or urine) evolve, liquid biopsies will be more effective and reliable tools for monitoring a patient with a cancer risk. In fact, urine, cerebrospinal fluid (CSF), blood plasma, blood or body fluid is a sample that is easily obtainable, and thus the simple and non-invasive collection thereof in a large quantity is possible through repeated sampling. Accordingly, in a cancer diagnosis, methods of detecting and analyzing pathogen DNA through a liquid biopsy, which is most non-invasive, are drawing attention.

However, with current technology, there are many limitations to early cancer diagnosis methods that involve analyzing cfDNA in a liquid sample (e.g., blood or urine) and finding a mutation produced in a gene (Korean Laid-open Patent Application No. 10-2016-0129523). In particular, cfDNA is present in a very low concentration in a sample such as urine, CSF, blood plasma, or blood, and a gene mutation, which may naturally take place during a process of cfDNA aging, does not necessarily lead to cancer, and, even if progressed to cancer, does not necessarily cause a serious problem. Therefore, a method for improving detection sensitivity and enhancing the accuracy of an early cancer diagnosis is urgently required.

Since cfDNA is found at an extremely low level in a liquid sample, developing a high-quality DNA extraction protocol based on a small amount of sample is the most important task in molecular analysis. It is expected that the use of a magnetic nanostructure according to the present invention will enable the establishment of techniques for the ultra-high sensitive detection, concentration, and isolation of cfDNA from a liquid sample such as urine, CSF, blood plasma, or blood.

SUMMARY OF THE INVENTION

The present inventor has prepared a magnetic nanostructure for detecting and isolating cell-free DNA (cfDNA) that includes a cationic polymer and a magnetic-nanoparticle-containing conductive polymer, and completed the present invention on the basis of a finding that the magnetic nanostructure is capable of efficiently detecting various types of cfDNA from a small amount of a biological sample such as urine, cerebrospinal fluid (CSF), blood plasma, blood or body fluid and has significantly improved performance in terms of the detection, isolation, and extraction of cfDNA, which is present in a trace amount in a sample.

Hence, an object of the present invention is to provide a magnetic nanostructure for detecting and isolating cfDNA that includes a cationic polymer and a magnetic-nanoparticle-containing conductive polymer.

Another object of the present invention is to provide a method of detecting and/or isolating cfDNA, the method using a magnetic nanostructure for detecting and isolating cfDNA that includes a cationic polymer and a magnetic-nanoparticle-containing conductive polymer.

Still another object of the present invention is to provide a composition for a cancer diagnosis, the composition including, as an active ingredient, a magnetic nanostructure for detecting and isolating cfDNA that includes a cationic polymer and a magnetic-nanoparticle-containing conductive polymer.

Yet another object of the present invention is to provide a cancer diagnosis kit including a magnetic nanostructure for detecting and isolating cfDNA that includes a cationic polymer and a magnetic-nanoparticle-containing conductive polymer.

An additional object of the present invention is to provide a method of providing information for diagnosing the onset and/or prognosis of cancer, the method using a magnetic nanostructure for detecting and isolating cfDNA that includes a cationic polymer and a magnetic-nanoparticle-containing conductive polymer.

Another additional object of the present invention is to provide a method of diagnosing cancer, the method using a magnetic nanostructure for detecting and isolating cfDNA that includes a cationic polymer and a magnetic-nanoparticle-containing conductive polymer.

However, technical objects of the present invention are not limited to those listed above, and other objects not mentioned above will be clearly understood by those skilled in the art from the following description.

To accomplish the aforementioned objects of the present invention, the present invention provides a magnetic nanostructure for detecting and isolating cfDNA that includes a cationic polymer and a magnetic-nanoparticle-containing conductive polymer.

In this case, the magnetic nanostructure is surface-treated with the cationic polymer.

In one embodiment of the present invention, the cationic polymer may be polyethyleneimine (PEI).

In another embodiment of the present invention, the cationic polymer and the conductive polymer may be prepared through binding between biotin and streptavidin.

In still another embodiment of the present invention, the conductive polymer may be polypyrrole or a derivative thereof.

In yet another embodiment of the present invention, the magnetic nanostructure may be a magnetic nanowire.

In additional embodiment of the present invention, the cfDNA may be separated from the magnetic nanostructure upon a change in pH.

Also, the present invention provides a method of detecting and isolating cfDNA, the method including: (1) a process of treating a sample with magnetic nanostructures for detecting and isolating cfDNA according to the present invention; (2) a process in which cfDNA included in the sample is attached to the magnetic nanostructures; (3) a process of isolating, from the sample, the magnetic nanostructures that include cfDNA attached thereto; and (4) a process of separating, by changing the pH, cfDNA from the magnetic nanostructures of the process (3), which include the cfDNA attached thereto.

In one embodiment of the present invention, the sample used in the method of detecting and isolating cfDNA may be urine, CSF, blood plasma, or blood.

Also, the present invention provides a composition for a cancer diagnosis that includes the magnetic nanostructure for detecting and isolating cfDNA according to the present invention as an active ingredient.

Also, the present invention provides a method of diagnosing cancer, the method comprising: extracting or separating cfDNA from the magnetic nanostructure according to claim 1; and analyzing the cfDNA.

In one embodiment of the present invention, the cancer may be cervical cancer, lung cancer, or breast cancer.

Also, the present invention provides a cancer diagnosis kit that includes the magnetic nanostructure for detecting and isolating cfDNA according to the present invention.

Moreover, the present invention provides a method of providing information for diagnosing the onset and/or prognosis of cancer, the method including a process of extracting or separating cfDNA from the magnetic nanostructure for detecting and isolating cfDNA according to the present invention and then analyzing the cfDNA.

In addition, the present invention provides a method of diagnosing cancer by using the magnetic nanostructure for detecting and isolating cfDNA according to the present invention.

The magnetic nanostructure for detecting and isolating cfDNA according to the present invention includes a cationic polymer and a magnetic-nanoparticle-containing conductive polymer, and can effectively detect various types of cfDNA from a small amount of a biological sample such as urine, CSF, blood plasma, or blood. More specifically, the magnetic nanostructure for detecting and isolating cfDNA according to the present invention can effectively capture cfDNA, which is present in a trace amount in a sample, due to a strong magnetic field generated from a large amount of magnetic nanoparticles included in the magnetic nanostructure during an electropolymerization process. Also, in detecting, isolating, and extracting cfDNA, the magnetic nanostructure can include a large amount of PEI, which is a cationic polymer, attached thereto by having a long magnetic nanowire structure, and thus has a greatly enhanced efficiency of capturing DNA present in a sample. Therefore, the use of the magnetic nanostructure results in enhanced detection sensitivity, which leads to significantly improved cfDNA detection and isolation as compared to the conventional art. Also, by having a thread-like thin and long structure, the magnetic nanowire can effectively detect and capture cancer-related cfDNA by penetrating through gaps among a large number of cells or protein molecules present in blood or urine, and thus exhibits a significantly improved detection efficiency. Therefore, it is expected that the magnetic nanostructure for detecting and isolating cfDNA according to the present invention will be used for extracting DNA from blood cancer cells for use in a genetic mutation diagnosis service, as well as for an early cancer diagnosis and cancer treatment.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIGS. 4A and 4B show a DNA detection limit (limit of detection: LOD) of PEI/mPpy NWs, which were surface-treated with a cationic polymer;

FIG. 5A compares HPV DNA genotyping results obtained from cell samples respectively by using the PEI/mPpy NWs according to the present invention and commercial Roche cobas 4800 HPV Test, wherein the cell samples were collected from a cervix of cervical cancer patients using a cotton swab;

FIG. 8 shows the DNA detection limit of the PEI/mPpy NWs according to the present invention in urine samples. Limit of detection (LOD) obtained for HPV DNA samples with HPV-16 and HPV-18 genotyping extracted by PEI/mPpy NWs. HPV-positive cell lines were ex vivo spiked into the HPV-negative urine pool to analyze the performance of the nanowire in DNA isolation;

FIG. 9B shows analysis results of HPV DNA genotyping profiles of cervical cancer patients;

FIGS. 10B and 10C show type-specific HPV detection form urine samples or cervical swab specimens;

FIG. 11F shows DNA mutations identified through PCR amplification after DNA isolation with the PEI/mPpy NWs according to the present invention and the commercial Qiagen Kit®;

FIG. 11I compares mutations in cfDNA and cancer tissues detected from blood plasma or cerebrospinal fluid (CSF) of lung cancer patients using the PEI/mPpy NWs according to the present invention.

DETAILED DESCRIPTION OF EXEMPLARY EMBODIMENTS

Figure 1A:
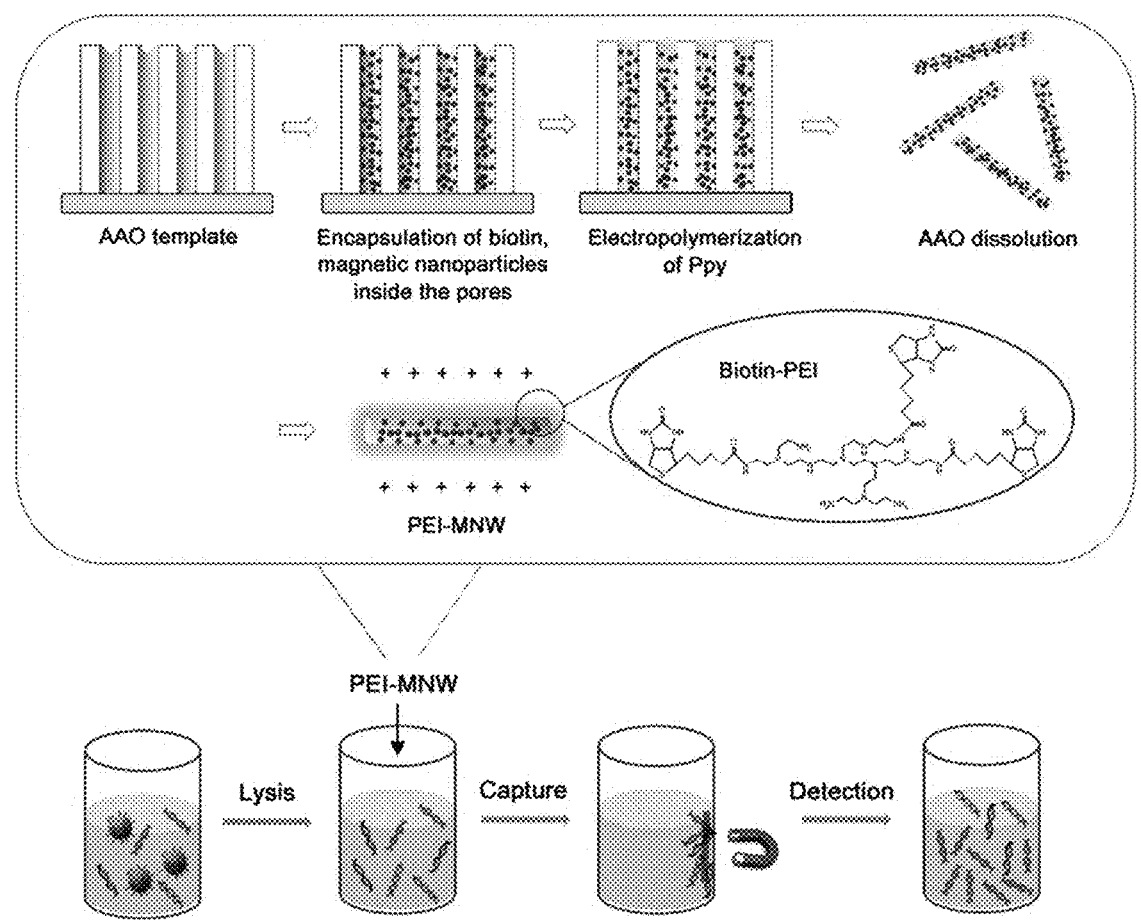
FIGS. 1A and 1B are schematic diagrams for illustrating a method of detecting and isolating cell-free DNA (cfDNA) by using magnetic nanostructures (PEI/mPpy NWs) according to the present invention, wherein the PEI/mPpy NWs include polyethyleneimine (PEI), which is a cationic polymer, attached to a surface thereof.

The present invention relates to a magnetic nanostructure for detecting and isolating cell-free DNA (cfDNA). Also, having been found to be able to effectively detect various types of cfDNA from a small amount of a biological sample such as urine, cerebrospinal fluid (CSF), blood plasma, or blood or body fluid, and have significantly improved performance in terms of the detection, isolation, and extraction of cfDNA present in a trace amount in a sample, the magnetic nanostructure according to the present invention will be useful for preventing, diagnosing, or treating cancer.

The present invention will be described in detail below.

The present invention provides a magnetic nanostructure for detecting and isolating cfDNA that includes a cationic polymer and a magnetic-nanoparticle-containing conductive polymer and is surface-treated with the cationic polymer.

The term "cell-free DNA or circulating cell-free DNA (cfDNA)" used herein refers to cancer-cell-derived DNA that is derived from a tumor cell and may be found in a biological sample such as urine, CSF, blood plasma, or blood collected from a cancer patient, and encompasses circulating tumor DNA (ctDNA) as well. For detailed observation of cancer development, metastasis, and the like, the cfDNA obtained from a biological sample such as urine, CSF, blood plasma, or blood may be analyzed by a non-invasive, non-surgical method of analyzing cancer-cell-derived DNA based on body fluid examination, which may be used as an alternative to existing invasive diagnostic and testing methods. Also, diagnosing cancer and monitoring the prognosis of a cancer patient may be possible through cfDNA detection.

The cationic polymer according to the present invention is not limited to a particular type, but is preferably polyethyleneimine (PEI) and more preferably a cationic branched PEI polymer.

Also, the cationic polymer and the magnetic nanostructure according to the present invention may be prepared through binding between biotin and streptavidin.

Moreover, the conductive polymer according to the present invention may be polypyrrole or a derivative thereof, but is not limited thereto. Pyrrole (Ppy) nanowires electrochemically doped with a high number of magnetic nanoparticles (MNPs) and biotin moieties are efficiently conjugated with highly cationic branched polyethyleneimine (PEI) via streptavidin-biotin interaction to obtain PEI-conjugated MNWs.

Furthermore, the magnetic nanostructure according to the present invention may be a magnetic nanowire, but is not limited thereto. The magnetic nanowire according to the present invention is doped with all of a large amount of magnetic nanoparticles, polypyrrole, which is a conductive polymer, and biotin during an electrochemical deposition process, which may ultimately result in the introduction of a large amount of the cationic branched PEI polymer onto the magnetic nanostructure. More specifically, the magnetic nanostructure is initially prepared into a form of a free-standing polypyrrole nanowire (Ppy NW) doped with magnetic nanoparticles and biotin molecules, followed by the addition of N-(3-dimethylaminopropyl)-N'-ethylcarbodiimide hydrochloride (EDC) and N-hydroxysuccinimide (NHS) onto the Ppy NW, activation of a carboxylic acid group (—COOH), and labeling with streptavidin. Subsequently, the nanowire labeled with streptavidin is added into a PEI solution containing biotin added thereinto, and cationic branched PEI is additionally conjugated onto the magnetic nanowire through a biotin-streptavidin interaction. As a result, magnetic nanoparticles may be irregularly distributed in and incorporated at high density into the magnetic nanostructure (PEI/mPpy NW), which includes the cationic PEI polymer conjugated on a surface thereof. Such a magnetic nanowire may be able to successfully capture genomic DNA with high efficiency even at low DNA concentrations. In particular, due to the nature of the magnetic nanowires arising from a large surface area for binding to a target molecule such as DNA, an improved mobility for promoting an interaction with DNA, and a high reactivity to an applied magnetic field, efficient, effective, and excellent contact and binding to target DNA may be induced through an electrostatic interaction.

In the present invention, the cfDNA may be human papillomavirus (HPV) DNA, but is not limited thereto. HPVs are double-helical DNA viruses that belong to the family of Papillomaviridae causing warts and cervical cancer upon human infection, and are the most common virus type causing an abnormality in an epithelium of skin and mucosa. Among the HPVs, high-risk carcinogenic HPVs are known to be highly associated with cervical cancer, and it has been reported that a high-risk HPV gene is inserted into a host genome, proliferates, and forms a tumor through a pre-cancer stage known as an epithelial tumor. In particular, HPV16 and HPV18 are detected from 90% or more of cervical intraepithelial neoplasia (CIN) tissues and squamous cell carcinoma (SCC) tissues. Therefore, HPV16 and HPV18 are most important among the carcinogenic HPVs and are found in 70% or more of cases of cervical cancer. In general, molecular diagnostics of HPV is mainly used to amplify genomic DNA extracted from a clinical sample to check for HPV infection. By confirming the presence of a particular gene sequence at a molecular level, the molecular diagnostics provides an important insight for the prediction and monitoring of disease progression. In fact, the efficient detection of a targeted genetic material not only identifies a fundamental mechanism of a disease but also facilitates treatment decisions based on collected information. However, methods based on real-time PCR used in conventional molecular diagnostics are limited in that the methods cannot provide an early diagnosis of HPV infection due to low clinical sensitivity and specificity. Currently, traditional cervical cytology is used as a method for screening HPV infection. Since such a conventional test method requires the harvesting of cells from a cervix, feelings of reluctance and discomfort caused thereby leads to a difficulty of periodic check-ups. However, periodic cervical cancer screening may prevent an incidence of cervical cancer by 60%. Therefore, performing proper, non-invasive, and less rejected cervical cancer screening by using a urine, CSF, blood plasma, or blood sample may be a key factor in preventing an incidence of cervical cancer and reducing mortality with low costs and high efficiency.

Therefore, the molecular diagnosis of HPV may be carried out based on cfDNA isolated following the ultra-high sensitivity detection of the cfDNA from a urine, CSF, blood plasma, or blood sample by using the magnetic nanostructure for detecting and isolating cfDNA according to the present invention.

Also, the cfDNA according to the present invention may be separated from the magnetic nanostructure upon a change in pH. More preferably, a significantly larger amount of DNA is captured in an acidic or neutral (pH 3 to 7) environment, and, likewise, a DNA separation efficiency significantly increases in a basic (pH 10) environment. Such correlations are caused by the protonation of an amine group ($NH_2$; pKa=7.11) in PEI at a low pH, resulting in the strengthening of an electrostatic interaction with a negatively charged phosphate group in DNA, thus ultimately maximizing the ability of the magnetic nanowires to have DNA attached thereto. When a pH-dependent release pattern of the DNA attached to magnetic nanowires was examined in a quantitative manner, it can be seen that the amount of the DNA separated from the magnetic nanowires significantly increased with an increase in pH. It was found that such a correlation is directly related to the deprotonation of an amine group in PEI and ultimately compromises the integrity of a DNA-PEI complex.

In another aspect, the present invention provides a method of detecting and/or isolating cfDNA. More specifically, the method of detecting and/or isolating cfDNA according to the present invention may include: (1) a process of treating a sample with magnetic nanostructures for detecting and isolating cfDNA according to the present invention; (2) a process in which cfDNA included in the sample is attached to the magnetic nanostructures; (3) a process of isolating, from the sample, the magnetic nanostructures that include cfDNA attached thereto; and (4) a process of separating, by changing the pH, cfDNA from the magnetic nanostructures of the process (3), which include the cfDNA attached thereto.

In the present invention, the sample may be a biological sample. Preferably, the sample is a liquid sample such as urine, CSF, blood plasma, or blood, but is not limited thereto.

In a still another aspect, the present invention provides a composition for a cancer diagnosis that includes the magnetic nanostructure for detecting and isolating cfDNA according to the present invention as an active ingredient.

Also, the cancer according to the present invention is not limited to a particular type, and may be any of various cancer types. Therefore, the cancer may be liver cancer, colon cancer, rectal cancer, lung cancer, endometrial cancer, ovarian cancer, renal pelvis cancer, pancreatic cancer, small intestine cancer, hepatopancreatobiliary cancer, gastric cancer, a brain tumor, breast cancer, or the like.

In a yet another aspect, the present invention provides a cancer diagnosis kit that includes the magnetic nanostructure for detecting and isolating cfDNA according to the present invention. More specifically, the cancer diagnosis kit may be a biosensor, but is not limited thereto.

In an additional aspect, the present invention provides a method of providing information for diagnosing the onset and/or prognosis of cancer. More specifically, the method of providing information for diagnosing the onset and/or prognosis of cancer according to may include a process of extracting or isolating cfDNA from the magnetic nanostructure for detecting and isolating cfDNA according to the present invention and analyzing the same, and the analysis may confirm the presence of a gene mutation by analyzing the concentration, number of copies, or base sequence of DNA in a sample.

In another additional aspect, the present invention provides a method of diagnosing cancer using the magnetic nanostructure for detecting and isolating cfDNA according to the present invention.

In one embodiment of the present invention, a magnetic nanostructure (PEI/mPpy NW) surface-treated with a PEI cationic polymer was prepared as the magnetic nanostructure for detecting and isolating cfDNA according to the present invention. When morphological characteristics of the magnetic nanostructure were evaluated, magnetic nanoparticles were found to be incorporated at high density into the magnetic nanostructure according to the present invention (see Example 1).

Also, to assess the DNA detection efficiency and DNA recovery efficiency of the PEI/mPpy NWs for detecting and isolating cfDNA according to the present invention in cervical swab specimens, DNA capture efficiency and DNA isolation efficiency as a function of pH were assessed (see Example 2-1), the DNA detection limit (LOD) of the PEI/mPpy NWs according to the present invention in cervical swab specimens was determined (see Example 2-2), and the HPV genotyping efficiency and DNA capture efficiency of the PEI/mPpy NWs according to the present invention and a commercial cobas 4800 HPV system in cervical swab specimens were compared (see Example 2-3).

Also, the DNA detection efficiency and DNA recovery efficiency of the PEI/mPpy NWs for detecting and isolating cfDNA according to the present invention in urine samples were assessed (see Example 3-1), the DNA detection limit (LOD) of the PEI/mPpy NWs according to the present invention in urine samples was determined (see Example 3-2), HPV DNA was extracted from urine samples using the PEI/mPpy NWs according to the present invention (see Example 3-3), and a pattern of HPV genotype distribution in urine samples of cancer patients or a healthy control group obtained by using the PEI/mPpy NWs according to the present invention was evaluated (see Example 3-4).

In addition, DNA detection efficiency of the PEI/mPpy NWs for detecting and isolating cfDNA according to the present invention in blood plasma samples was assessed (see Example 4-1), DNA capture efficiency of the PEI/mPpy NWs as a function of PEI/mPpy NW length in blood plasma samples was assessed (see Example 4-2), DNA detection efficiencies of the PEI/mPpy NWs and a Qiagen Kit® in blood plasma samples were compared (see Example 4-3), DNA detection efficiencies of the PEI/mPpy NWs and the Qiagen Kit® in blood plasma samples of breast cancer or lung cancer patients were compared (see Example 4-4), and mutations in DNA extracted with the PEI/mPpy NWs and the Qiagen Kit® from blood plasma samples of lung cancer patients were identified (see Example 4-5). Also, DNA detection efficiency of the PEI/mPpy NWs for detecting and isolating cfDNA according to the present invention in blood plasma or CSF samples was assessed (see Example 4-6).

The magnetic nanostructure for detecting and isolating cfDNA according to the present invention can significantly improve detection and extraction efficiencies of DNA present in a urine, CSF, blood plasma, or blood sample, and exhibits an enhanced sensitivity. Therefore, it is expected that the magnetic nanostructure for detecting and isolating cfDNA according to the present invention will be used for extracting DNA for use in a genetic mutation diagnosis service as well as for an early cancer diagnosis and cancer treatment.

Exemplary embodiments of the present invention will be described below to help understanding of the present invention. However, the following exemplary embodiments are provided merely to facilitate understanding of the present invention, and should not be understood as limiting the scope of the present invention.

EXAMPLES

Figure 1B:
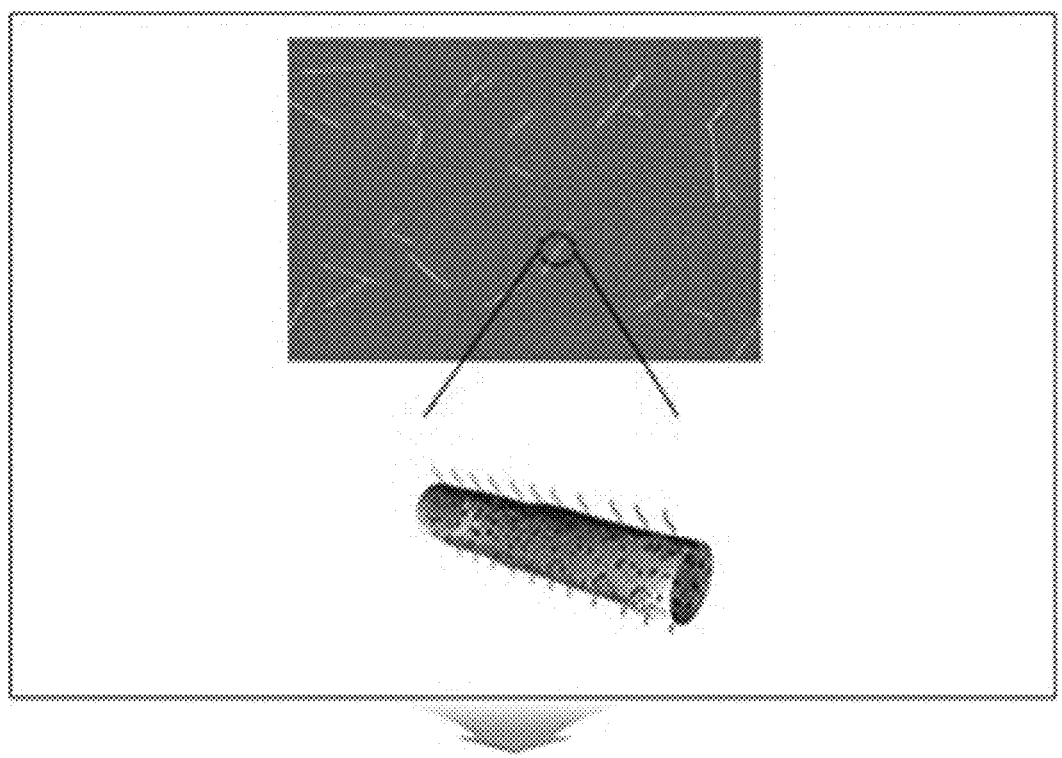
Figure 1B:
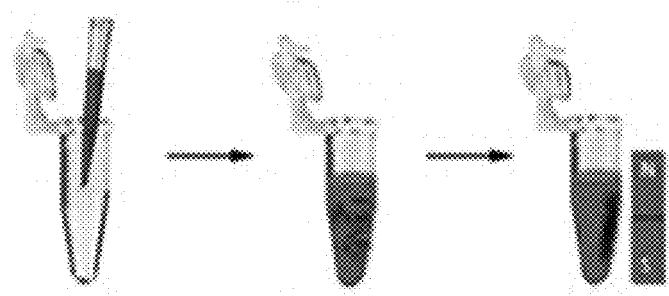

Example 1. Preparation and Morphological Evaluation of Magnetic Nanostructures (PEI/mPpy NWs) Surface-Treated with Cationic Polymer 1-1. Preparation of PEI/mPpy NWs As shown in FIGS. 1A and 1B, a magnetic nanostructure including polyethyleneimine (PEI), which is a cationic polymer, conjugated onto a surface thereof was prepared. One surface of an AAO template was coated with a gold (Au) layer (about 150 nm thick) for 600 seconds at $5 \times 10^{-3}$ mbar and 50 mA using the Q150T Modular Coating System (Quorum Technologies Ltd., UK). All electrochemical experiments were carried out on an Au-coated AAO template by using the BioLogic SP-150 potentiostat/galvanostat equipped with a platinum wire counter electrode and an Ag/AgCl (3.0 M NaCl type) reference electrode. In order to induce the attachment of magnetic nanoparticles (MNPs, 5 μg/ml, diameter: 10 nm) on the Au-coated AAO disk to prepare PEI/mPpy NWs, MNPs were prepared and were allowed to penetrate into pores of AAO through the application of suitable suction at room temperature (RT). 0.01 M poly(4-styrene sulfonic acid), a 0.01 M pyrrole solution containing 1 mg/ml biotin, and seven minutes of chronoamperometry at 1.0 V (vs. Ag/AgCl) were applied into the pores of the AAO template to perform electrochemical deposition. The AAO template thus processed was washed several times with distilled water, dipped in a 2 M sodium hydroxide (NaOH) solution for three hours, and then was put in Bioruptor® UCD-200 (Diagenode Inc.) for sonication to obtain free-standing polypyrrole (Ppy) nanowires (free-standing Ppy NWs) doped with MNPs and biotin molecules. Then, 30 mM N-(3-dimethylaminopropyl)-N'-ethylcarbodiimide hydrochloride (EDC) and 6 mM N-hydroxysuccinimide (NHS) were added to the resulting Ppy NWs prepared above to activate a carboxylic acid group (—COOH). Subsequently, the Ppy NWs were then incubated with streptavidin (10 μg/ml) for 45 minutes and were washed with distilled water. Then, the Ppy NWs labeled with streptavidin were put in a PEI solution containing biotin added thereinto, maintained additionally for one hour at room temperature, washed with water, and then were subjected to magnetic separation using a magnetic field. The PEI/mPpy NWs were dispersed in deionized water and stored at room temperature until use. With the above preparation method being used, individual Ppy NWs were released from the AAO template after the AAO template selectively dissolved, and cationic branched PEI (25 kDa) was additionally conjugated to the Ppy NWs through a biotin-streptavidin interaction.

1-2. Morphological Evaluation of PEI/mPpy NWs

The morphology of PEI/mPpy NWs was evaluated using a scanning electron microscope (SEM, JSM-7800F, JEOL Ltd.) and a transmission electron microscope (TEM, Tecnai™ G2F30, FEI). Magnetic force was measured with a SQUID-VSM magnetometer (MPMS VSM, Quantum Design, Inc.). Also, the surface charge of the PEI/mPpy NWs was measured with a zeta potentiometer (Zetasizer Nano ZS, Malvern Instruments Ltd.).

Figure 2A:
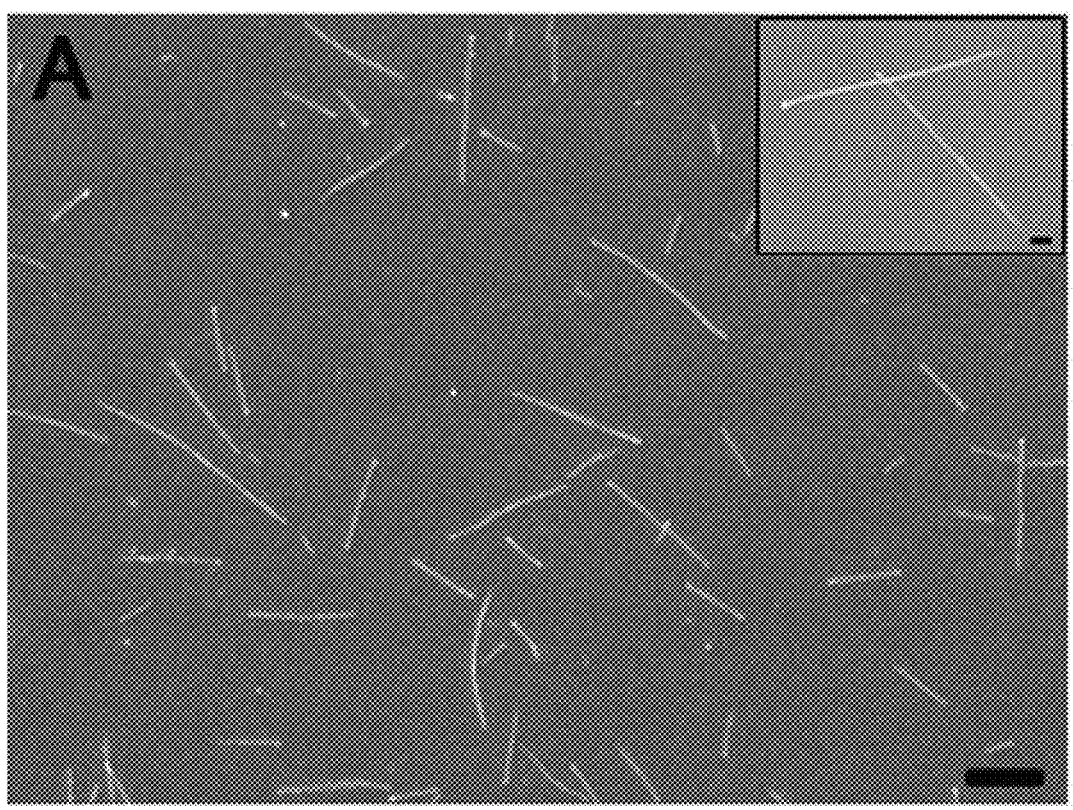
FIG. 2A is a scanning electron microscopic (SEM) image of the PEI/mPpy NWs according to the present invention.
Figure 2B:
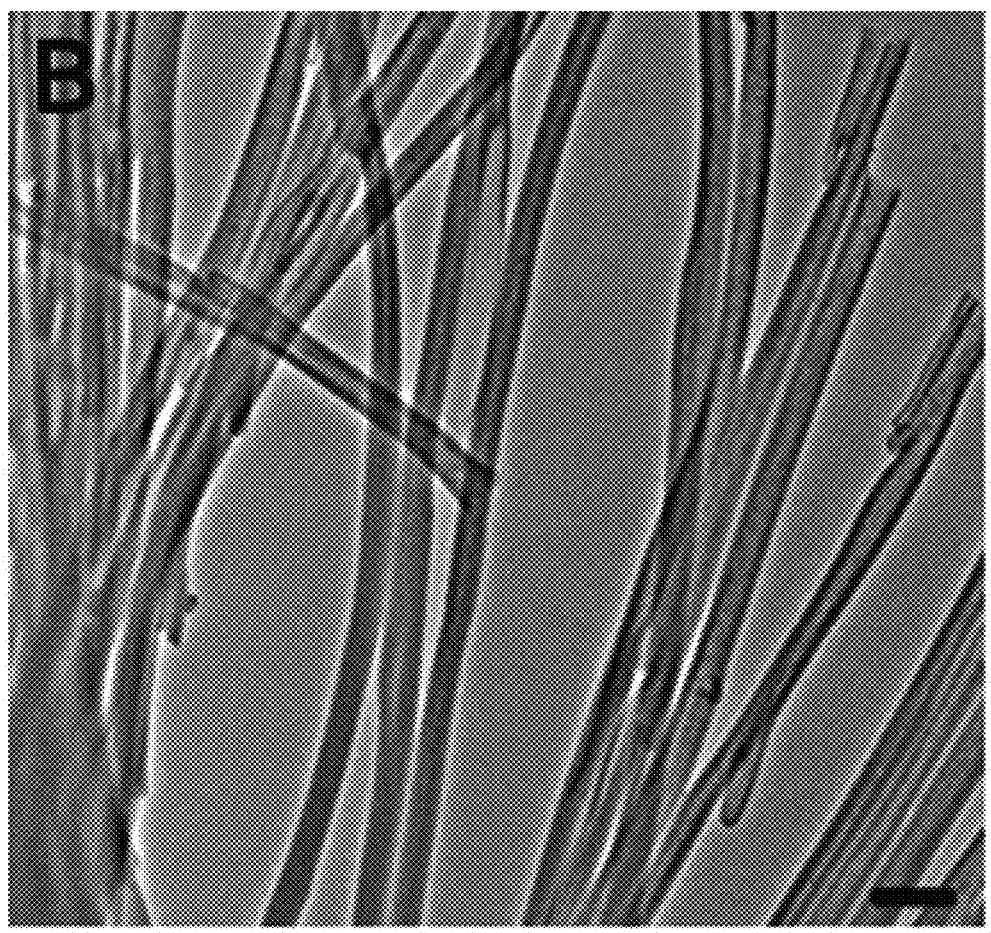
FIGS. 2B and 2C are transmission electron microscopic (TEM) images of the PEI/mPpy NWs according to the present invention.

An SEM image (scale bar: 10 μm, scale bar of enlarged view: 1 μm) in FIG. 2A and a TEM image (scale bar: 500 nm) in FIG. 2B confirm the synthesis of relatively long PEI/mPpy NWs with a diameter of about 200 nm and an average length of about 16 μm. It is also found that the PEI/mPpy NWs have a relatively wide length distribution. Such a long form of the Ppy NWs ensures a greater flexibility and versatility.

Figure 2C:
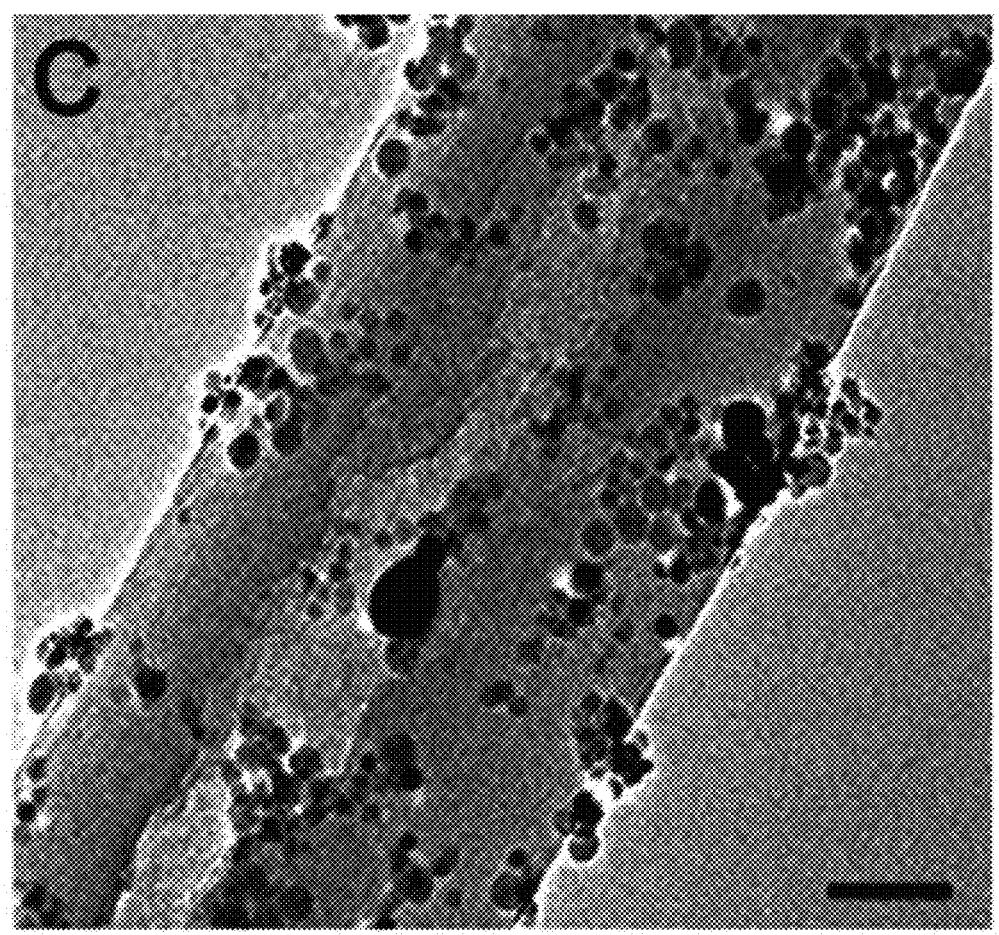

Also, a TEM image (scale bar: 50 nm) in FIG. 2C shows that the MNPs (diameter: <10 nm) are irregularly distributed and incorporated at high density in the PEI/mPpy NWs.

Figure 2D:
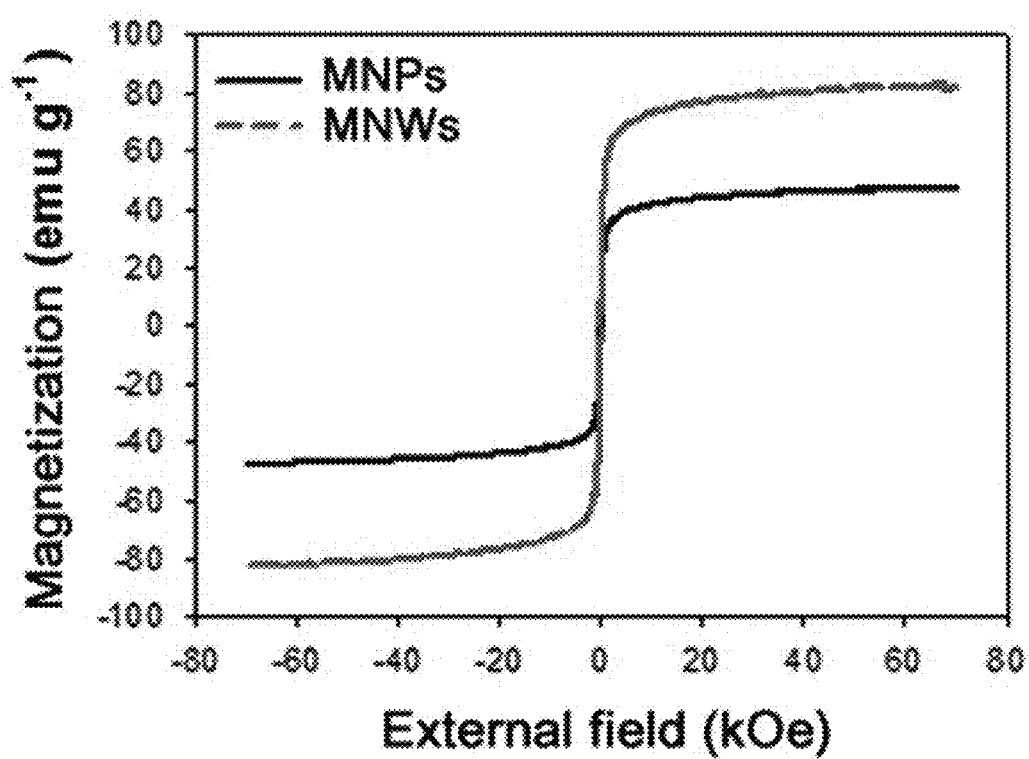
FIG. 2D shows magnetic hysteresis loops (magnetization curves) of the PEI/mPpy NWs according to the present invention and magnetic nanoparticles (MNPs)

Also, as shown in FIG. 2D, saturation magnetization values of the MNPs and PEI/mPpy NWs (PEI-MNWs) were measured and a magnetization curve thereof was plotted, results of which show that, when the number of MNPs bound to nanowires in the PEI/mPpy NWs and the number of MNPs tested for saturation magnetization are the same, the magnetization behavior of the PEI/mPpy NWs (saturation magnetization=82 emu/g) is more prominent than the magnetization behavior of the MNPs (saturation magnetization=45 emu/g). In particular, the magnetic force of the PEI/mPpy NWs was reinforced by the geometric confinement of iron oxide nanoparticles present at high density in the PEI/mPpy NWs and resulting alignment of magnetic moments of individual MNPs.

Figure 2E:
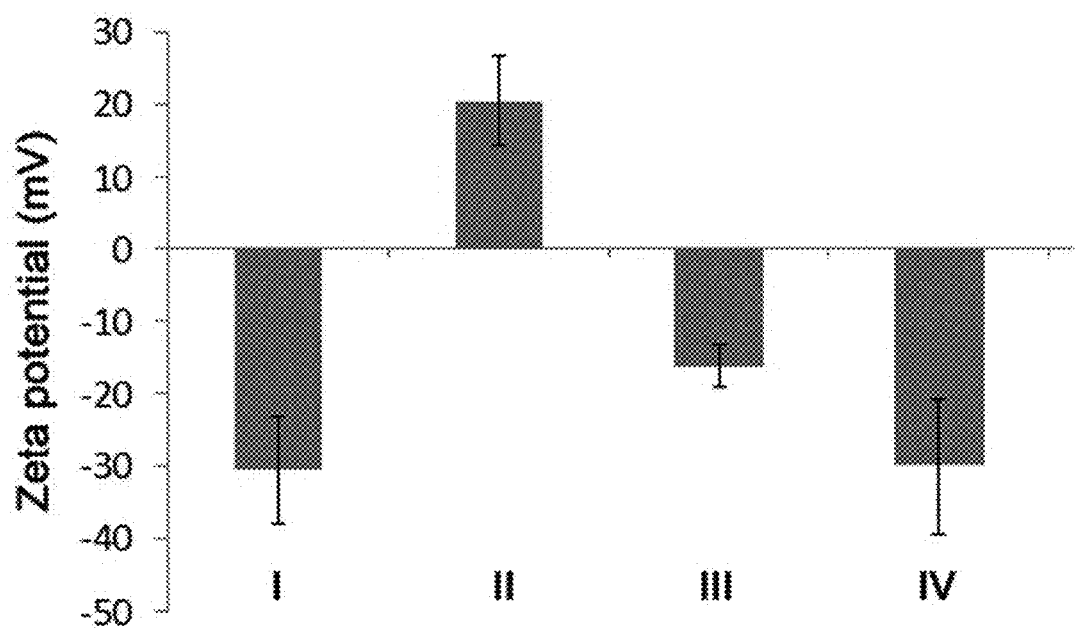
FIG. 2E shows zeta potential values determined for monitoring changes in surface charge during a process of DNA attachment to the PEI/mPpy NWs according to the present invention and DNA separation from the PEI/mPpy NWs.

Also, as shown in FIG. 2E, when zeta potential values were examined for monitoring changes in surface charge during DNA capture and recovery, zeta potential changed from positive (+) (II) to negative (−) (III) as a result of DNA attachment to the PEI/mPpy NWs. When the DNA captured by the PEI/mPpy NWs was separated later upon a change in pH, the zeta potential clearly decreased to a value (IV) similar to the zeta potential of pure DNA (I). In this case, (II), (III), and (IV) represent zeta potential values of PEI/mPpy NWs, a DNA-PEI/mPpy NW complex, and the DNA released from the DNA-PEI/mPpy NW complex at pH 10 (pure DNA is eluted), respectively.

Example 2. Efficiency Assessment of PEI/mPpy NWs in Cervical Swab Specimens

2-1. Assessment of DNA Capture Efficiency and DNA Recovery Efficiency of PEI/mPpy NWs as Function of pH To confirm an applicability of the PEI/mPpy NWs to DNA isolation, the DNA capture efficiency and DNA recovery efficiency of the PEI/mPpy NWs were evaluated. The evaluation was carried out by isolating genomic DNA from HeLa cells (HPV18-positive) or SiHa cells (HPV16-positive), both of which are HPV-positive cell lines, and spiking the genomic DNA of a known concentration with phosphate-buffered saline (PBS) ex vivo. More specifically, the genomic DNA recovered from the HeLa cells or SiHa cells was put in Tris-EDTA buffer (10 mM) at various concentrations (0.01 to 1000 ng/ml). For immediate DNA capture, the PEI/mPpy NWs (5 μl, 0.05 mg/100 μl) prepared according to Example 1 was added into a solution containing genomic DNA, and the mixture was gently shaken at room temperature for one hour. After the mixture was placed in a magnetic rack for 30 minutes, any unbound or nonspecifically bound substances were isolated. The DNA that had been captured by the PEI/mPpy NWs was subjected to vortexing in 10 mM Tris-HCl buffer (pH 10.0) at room temperature for one hour for DNA release. The DNA captured and then released was quantified through the PicoGreen assay in accordance with the manufacturer's instruction, and the captured DNA was confirmed by confocal microscopy.

Figure 3A:
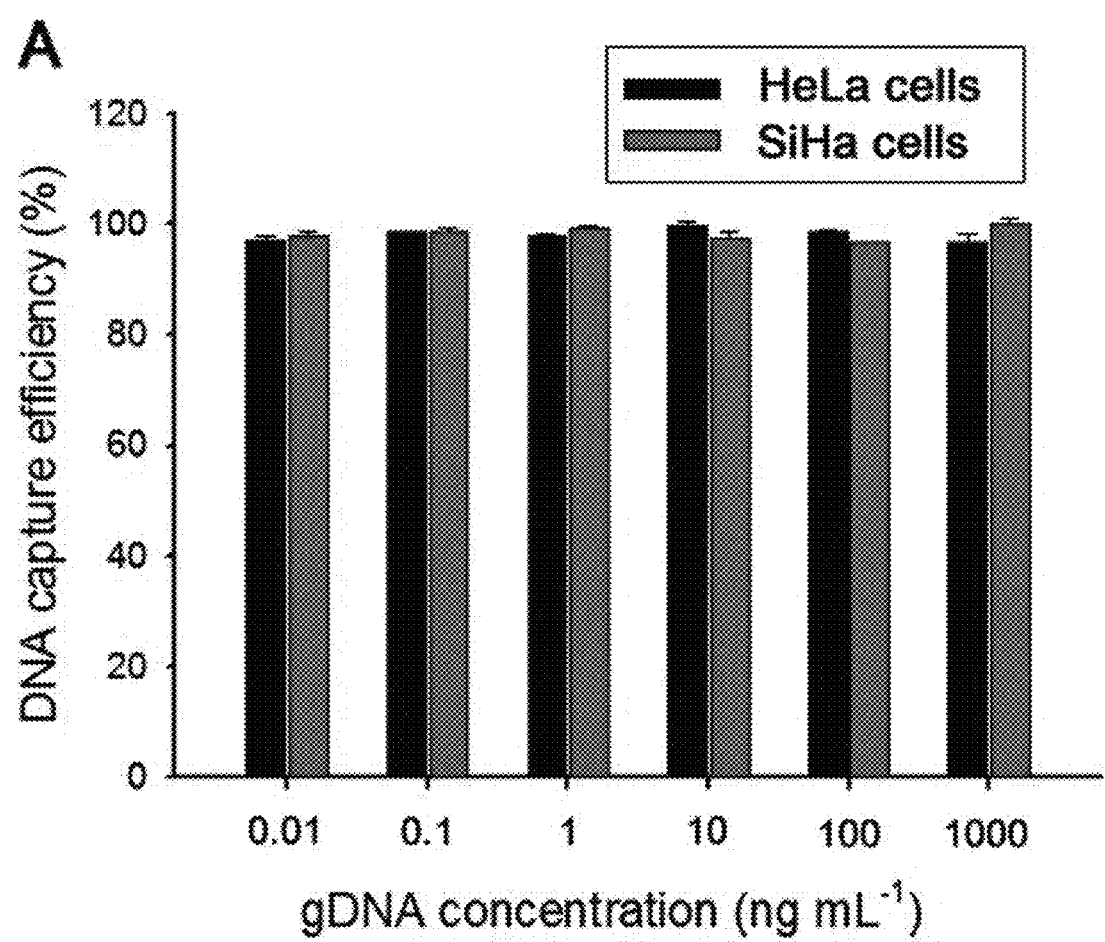
FIG. 3A shows a high genomic DNA recovery efficiency of the PEI/mPpy NWs according to the present invention.

Results as shown in FIG. 3A confirm excellent DNA recovery by the PEI/mPpy NWs irrespective of an input amount of the genomic DNA, and it is found that the PEI/mPpy NWs successfully captured the genomic DNA at an efficiency of 95% or more, even at a low genomic DNA concentration of 10 pg/ml. It is also found that, due to the nature of the PEI/mPpy NWs arising from a large surface area for binding to a target molecule, an improved mobility for promoting an interaction with DNA, and a high reactivity to an applied magnetic field, efficient, effective, and excellent contact and binding to target DNA may be induced through an electrostatic interaction.

Figure 3B:
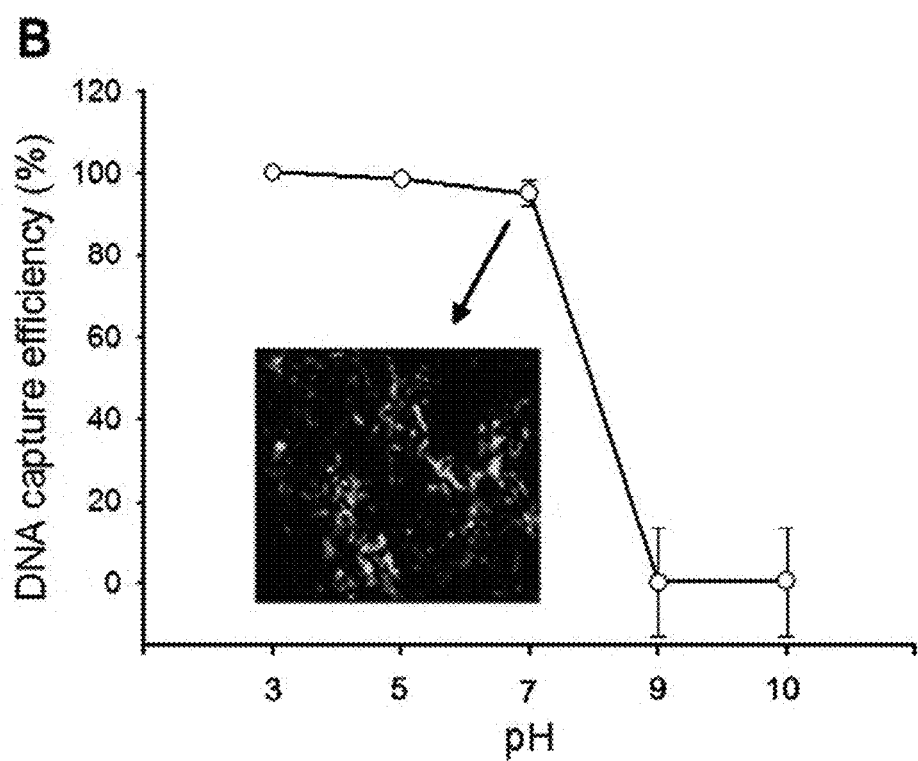
FIGS. 3B and 3C are confocal fluorescence images for directly identifying DNA recovered through being captured by the PEI/mPpy NWs according to the present invention.
Figure 3C:
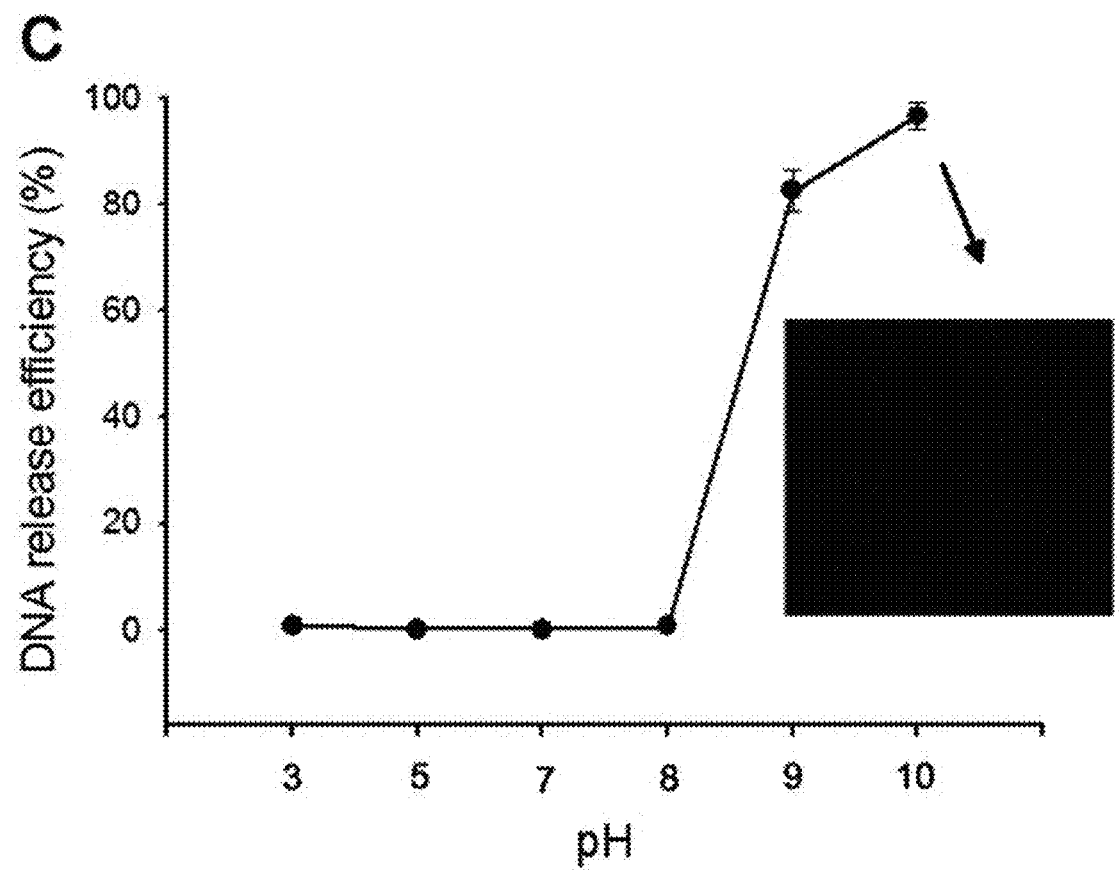

Also, as shown in FIGS. 3B and 3C, the DNA captured by the PEI/mPpy NWs and then recovered was directly viewed through DNA staining with PicoGreen and confocal fluorescence imaging. It is found, after storing the DNA-PEI/mPpy NW complex at pH 10, that all of the DNA that was captured was separated from the PEI/mPpy NWs. Also, DNA capture significantly improves under an acidic or neutral environment (pH 3 to 7) (FIG. 3B). Such correlations are caused by the protonation of an amine group ($NH_2$; pKa=7.11) in PEI at a low pH, resulting in the strengthening of an electrostatic interaction with a negatively charged phosphate group in DNA, thus ultimately maximizing the ability of the PEI/mPpy NWs to have DNA attached thereto. When a pH-dependent release pattern of the DNA attached to the PEI/mPpy NWs was examined in a quantitative manner, it can be seen that the amount of the DNA separated from the PEI/mPpy NWs significantly increased with an increase in pH (FIG. 3C). It is found that such a correlation is directly related to the deprotonation of an amine group in PEI and ultimately compromises the integrity of the DNA-PEI/mPpy NW complex. The PicoGreen reagent produces a clear green signal upon specific binding to double-stranded DNA, and serves as a clear indicator of DNA capture and DNA recovery by the PEI/mPpy NWs. At pH 7, strong green fluorescence is seen in a confocal image of the PEI/mPpy NWs, indicating a direct DNA attachment onto a surface of the PEI/mPpy NWs. In contrast, charge inversion occurs in the PEI/mPpy NWs at pH 10, leading to DNA separation, and thus no fluorescence signal is observed. Data presented are expressed as mean±standard deviation of five independent experiments.

2-2. Determination of DNA Detection Limit (LOD) of PEI/mPpy NWs in Cervical Swab Specimens To determine the DNA detection limit of the PEI/mPpy NWs, genomic DNA was isolated from HeLa cells (HPV18-positive) or SiHa cells (HPV16-positive), both of which are HPV-positive cell lines, and the genomic DNA of a known amount was spiked with PBS ex vivo in the same manner as described in Example 2-1. More particularly, the limit of detection (LOD) of various densities of cells was determined to analyze by adding HPV-18-positive HeLa (10-50 copies/cell) cells and HPV-16-positive SiHa (1-2 copies/cell) cells to HPV-negative urine pool. In general, the LOD was defined as the lowest concentration of HPV DNA detected with positive test results of at least 95% based on threshold cycle (Ct) values.

Figure 4B:
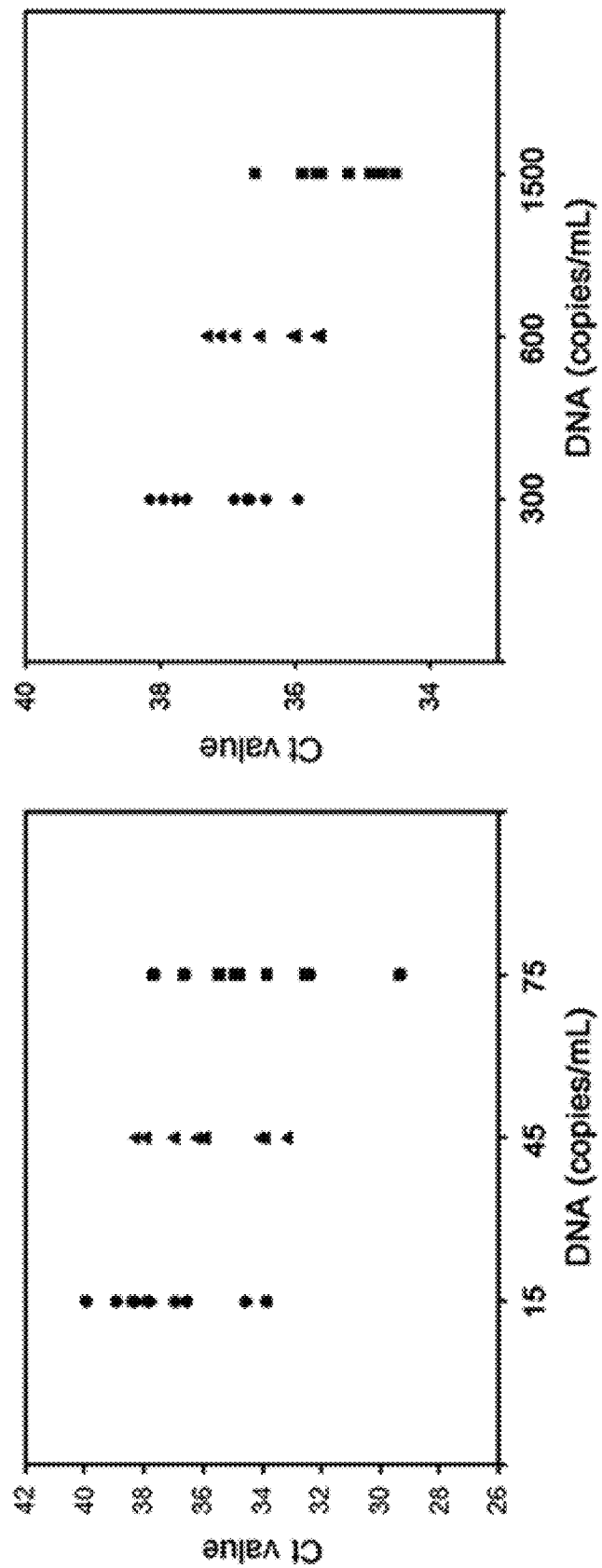

Results as summarized in FIG. 4A show that the HPV16/18 DNA detection limit of the PEI/mPpy NWs is 3 cells/ml. Similarly, the genomic DNA isolated from a SiHa cell line (left) and a HeLa (right) cell line as shown in FIG. 4B was added into PBS, and Ct values were plotted for each DNA amount. It is found that the Ct value of the DNA recovered from the PEI/mPpy NWs decreased as a function of the input amount of the genomic DNA isolated from the SiHa cell line (left) and HeLa (right) cell line. Such results signify that the PEI/mPpy NWs significantly improve analytical sensitivity, quantitative accuracy, and reproducibility and thus are appropriate for DNA capture and DNA recovery. In particular, a DNA detection efficiency at an extremely low HPV DNA level greatly improves.

2-3. Comparison of HPV Genotyping and DNA Capture Efficiency of PEI/mPpy NWs and Cobas 4800 HPV System in Cervical Swab Specimens Since the incidence of HPV-related cancers is rapidly increasing, it is judged that a more sensitive and specific detection strategy of HPV genotypes, particularly of high-risk HPV16 and HPV18, is applicable to a clinical diagnosis and treatment of a disease. Therefore, there is a need for verifying a clinical applicability of the PEI/mPpy NWs prepared according to Example 1 by evaluating an HPV DNA extraction efficiency of the PEI/mPpy NWs in cervical swab specimens collected from a cervix of cervical cancer patients and identifying various HPV genotypes such as HPV16, HPV18, and 12 other types, results of which were compared to Roche cobas 4800 HPV Test results. More specifically, to compare the PEI/mPpy NWs prepared according to Example 1 and the FDA-approved cobas 4800 HPV system in terms of DNA capture efficiency, cervical swab specimens were treated with sterile PBS, and were subjected to amplification through real-time PCR followed by multiple HPV genotyping. The cervical swab specimens were sampled from cervical cancer patients from the National Cancer Center (NCC; Goyang, Korea). All specimens were brought together in cobas PCR Cell Collection Media (Roche Molecular Systems, Inc.) and stored at 4° C. until tested. For the multiple HPV genotyping of the specimens, the cobas 4800 HPV Test was carried out through real-time PCR by using the cobas x 480 Instrument and cobas z 480 Analyzer. To extract HPV DNA with the cobas x 480 Instrument, each sample (400 μl) was lysed with a chaotropic reagent while increasing temperature. The HPV DNA was extracted with magnetic glass particles from a cell lysate and purified, and was eluted with an elution buffer (150 μl). Subsequently, the eluate (25 μl) was added into an equal volume of a PCR master mix, and was subjected to amplification with the cobas z 480 Analyzer. Likewise, HPV DNA was extracted from each sample (300 μl) by using the PEI/mPpy NWs: For cell lysis, glass beads (80 mg) were put into each sample (300 μl), the PEI/mPpy NWs (5 μl, 0.05 mg/100 μl) were immediately added into the mixture, which was then subjected to vortexing for one hour. HPV DNA was eluted with nuclease-free water (58 μl), and the DNA (13 μl) thus eluted was mixed with an equal volume of a cobas HPV master mix, which was then subjected to amplification with Roche LC480.

For HPV DNA genotyping from cervical swab specimens collected from a cervix of cervical cancer patients, results obtained respectively by using the PEI/mPpy NWs and Roche cobas 4800 HPV Test were mutually compared as shown in FIG. 5A. The Roche cobas 4800 HPV Test, which is an FDA-approved DNA amplification kit that makes use of real-time PCR, offers clinical sensitivity, specificity, and strong reproducibility for multiple HPV genotyping. Genomic DNA was extracted (isolated) with the PEI/mPpy NWs from cervical swab specimens obtained from cervical cancer patients, DNA was collected in a liquid-based cell culture medium, and quantitative real-time PCR amplification was performed to directly confirm the presence of HPV16, HPV18, and 12 other genotypes. The analytical sensitivity for the above three groups of HPV was determined with reference to analytical sensitivity results of the Roche cobas HPV Test. In particular, the HPV DNA results obtained respectively by using the PEI/mPpy NWs and the Roche cobas 4800 HPV Test are highly correlated. Also, as compared to the Roche cobas 4800 HPV Test results, in the case of the DNA extracted with the PEI/mPpy NWs, the Ct values of the target genes are significantly lower. In some cases, the Ct values of the PEI/mPpy NWs and the Roche cobas 4800 HPV Test are different from each other by eight cycles, indicating that there is about a 256-fold difference in a target DNA amount in samples.

Figure 5B:
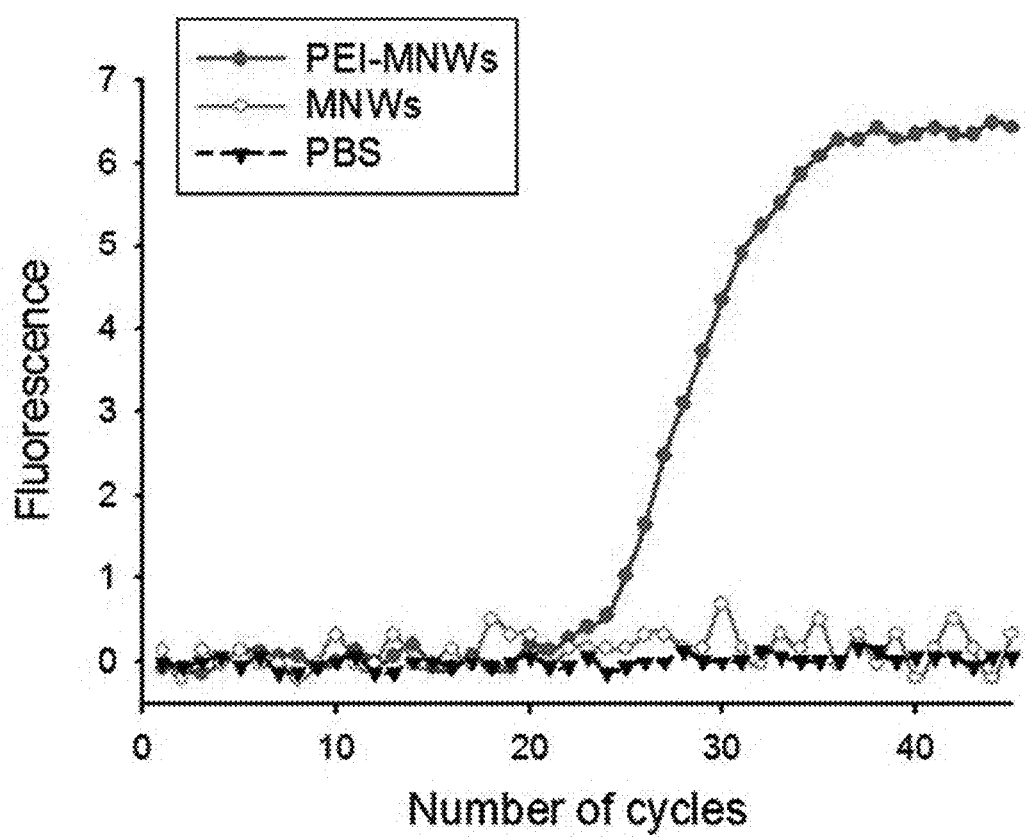
FIG. 5B illustrates the representative amplification of DNA extracted from cervical specimens obtained from cervical cancer patients.

FIG. 5B shows a representative plot for illustrating the amplification of DNA isolated from a cervical swab specimen of a patient (P4) in FIG. 5A. More specifically, when the PEI/mPpy NWs according to the present invention are used, excellent HPV DNA extraction and target-gene-specific signal amplification are observed. However, with magnetic nanowires free of PEI (appears green in FIG. 5B), gene amplification does not occur and HPV DNA is not detected. Such results signify that the PEI/mPpy NWs are capable of high-efficiency HPV DNA capture and analysis in cervical swab specimens, and may effectively capture, extract, and analyze multiple HPV DNA genotypes with higher sensitivity and specificity as compared to the Roche cobas 4800 HPV Test. Therefore, the PEI/mPpy NWs according to the present invention may provide meaningful results in the early detection and treatment of HPV-related cancers, thus improving diagnostic and therapeutic efficacy for HPV-related cancer patients.

Example 3. Efficiency Assessment of PEI/mPpy NWs in Urine Samples

Figure 6:
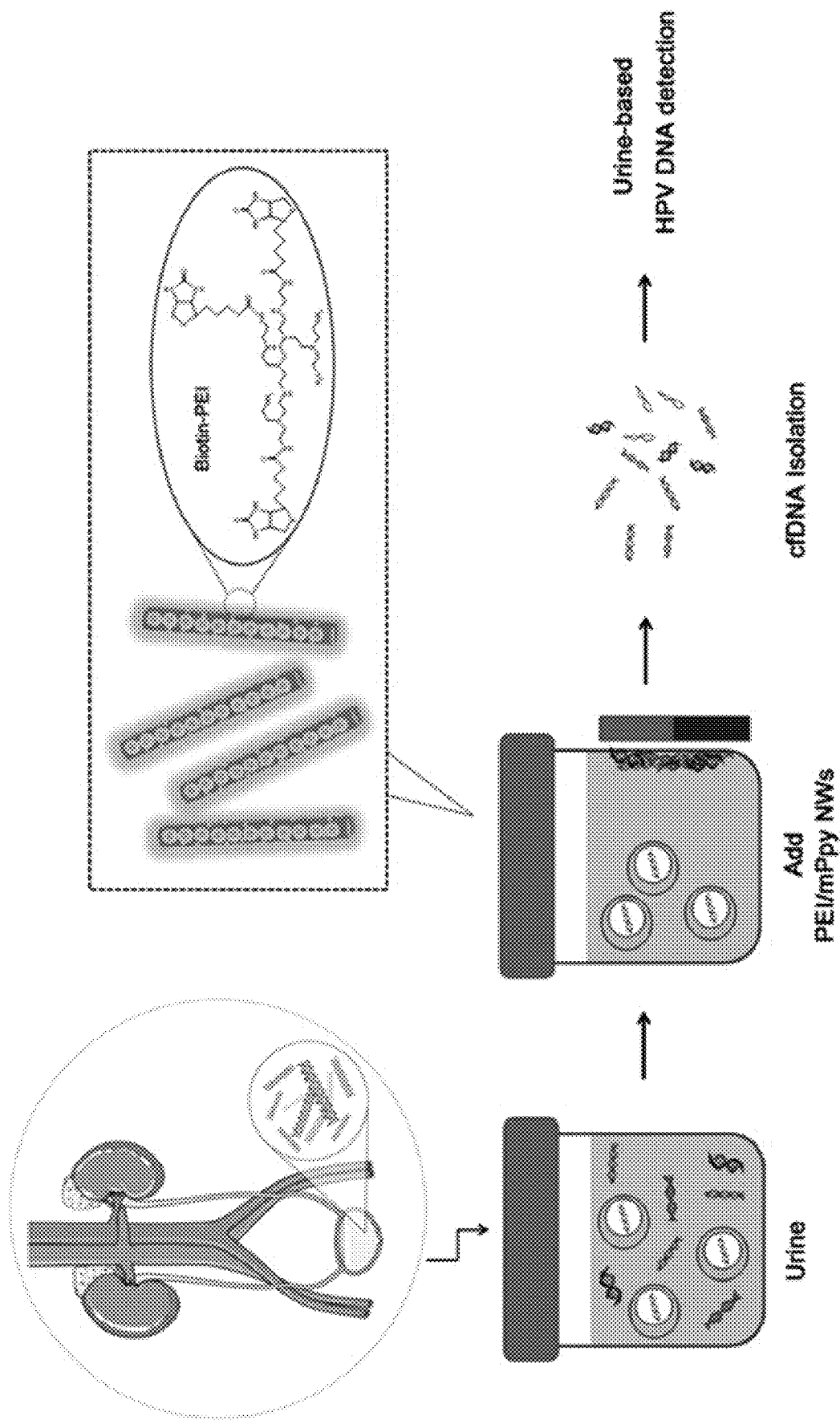
FIG. 6 is a conceptual diagram for illustrating a method of detecting and isolating cfDNA from a urine sample by using PEI-conjugated magnetic Ppy nanowires (PEI/mPpy NWs) according to the present invention, which include cationic PEI polymer attached to a surface thereof.

3-1. Assessment of DNA Capture Efficiency and DNA Recovery Efficiency of PEI/mPpy NW in Urine Samples To assess the DNA capture efficiency and DNA recovery efficiency of the PEI/mPpy NWs in a urine sample as illustrated in FIG. 6, the PEI/mPpy NWs were prepared according to Example 1. In this case, biotin-introduced PEI with a varying molecular weight (800 or 25000 Da) was added onto nanowires labeled with streptavidin for one hour at room temperature. Urine samples were collected from 30 HPV-positive patients and five healthy volunteers in accordance with an approval procedure of the Institutional Review Board of the NCC. The urine samples thus collected were stored at −20° C. until use. A known amount of the genomic DNA obtained from HPV18-positive (HeLa) cells or HPV16-positive (SiHa) cells was spiked with a HPV-negative urine sample ex vivo at a concentration in a range of 0.01 to 1,000 ng/ml. Subsequently, 0.5 mg/ml PEI/mPpy NWs were added into 300 µl of a urine sample containing the genomic DNA, and the mixture was stirred at 1,000 rpm for various durations (10, 30, 60, or 90 minutes). After the mixture thus stirred was placed in a magnetic rack for 30 minutes, any unbound or nonspecifically bound substances were isolated. Then, the DNA that had been captured was subjected to shaking at a maximum rate of 2,500 rpm for various durations (10, 30, 60, or 90 minutes), and then were eluted with 10 mM Tris-HCl buffer (pH 10.0). The DNA captured and then recovered was quantified through the PicoGreen assay in accordance with the manufacturer's instruction.

Figure 7A:
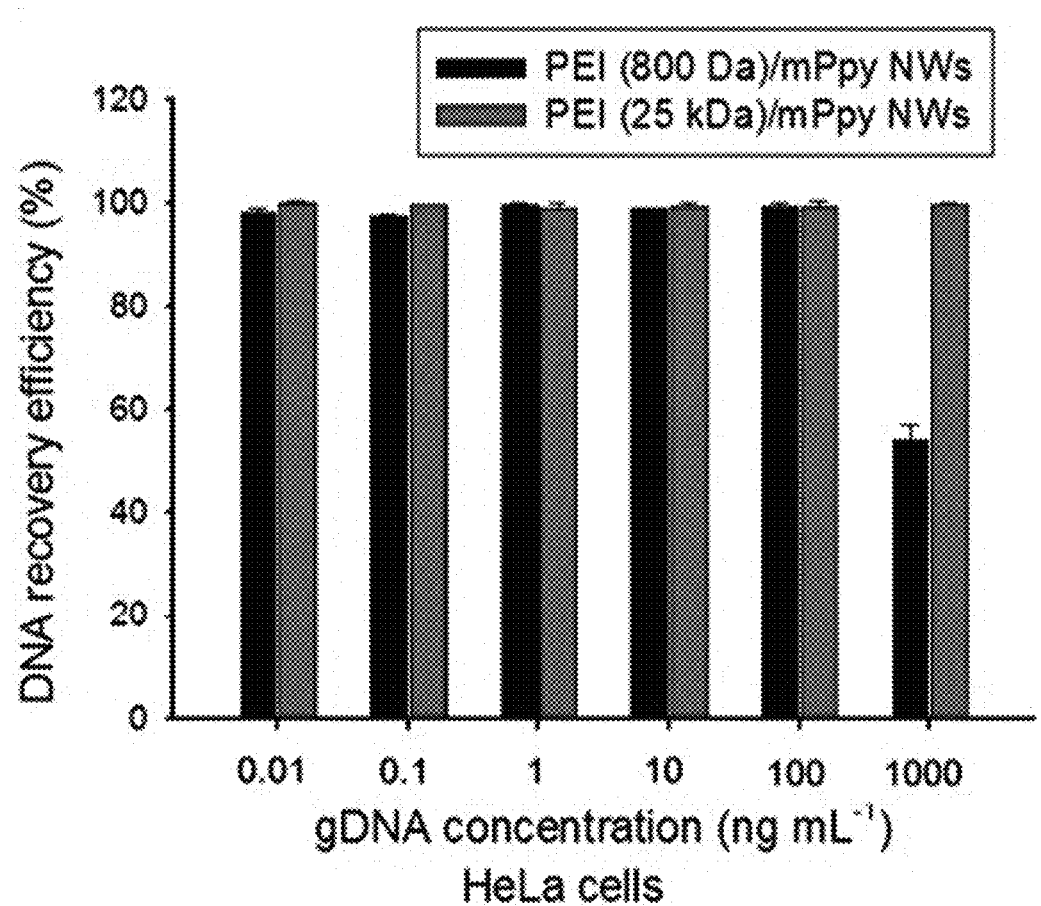
FIGS. 7A and 7B show a cfDNA recovery efficiency of the PEI/mPpy NWs according to the present invention when genomic DNA obtained from HPV18-positive (HeLa) cells or HPV16-positive (SiHa) cells was ex vivo spiked into the HPV-negative urine pool, where PEI/mPpy NWs were conjugated with branched PEI of different molecular weights of 800 Da and 25 kDa.
Figure 7B:
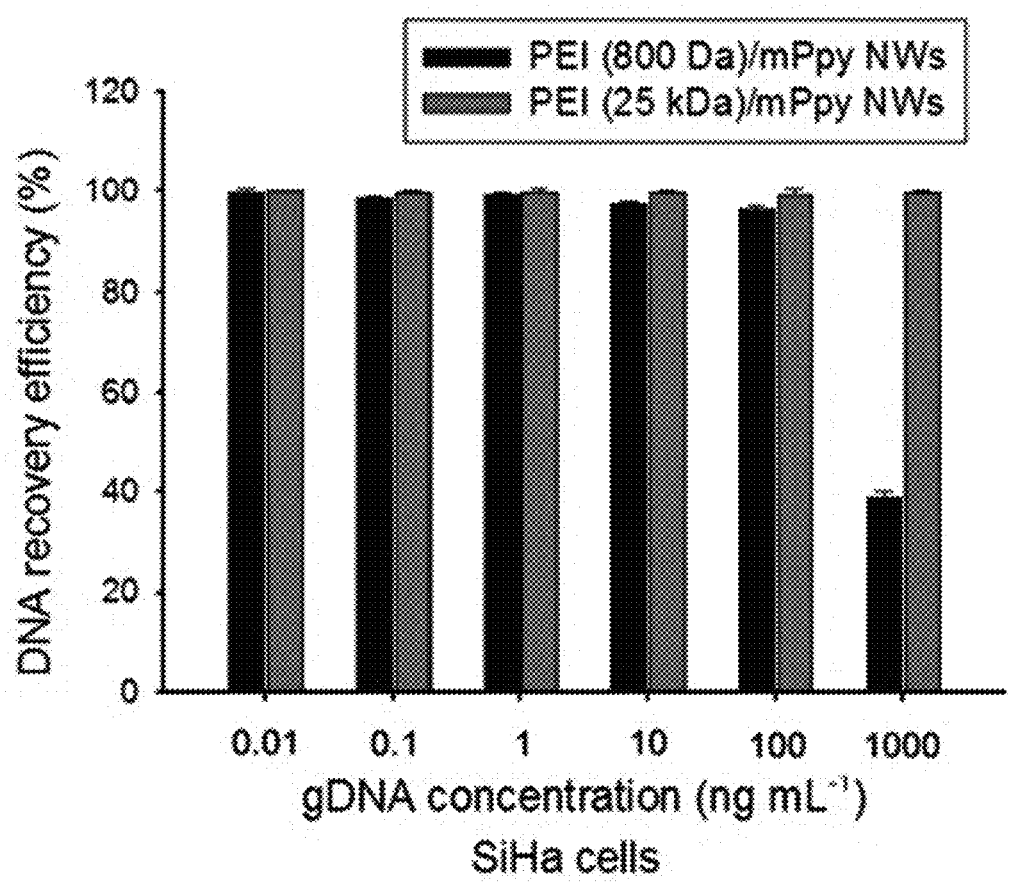

As illustrated in FIGS. 7A and 7B, when the genomic DNA obtained from HPV18-positive (HeLa) cells or HPV16-positive (SiHa) cells was mixed with an HPV-negative urine sample to evaluate the performance of the PEI/mPpy NWs with a varying PEI molecular weight (800 Da or 25 kDa). It is found that DNA recovery with a 90% or higher DNA capture efficiency and DNA recovery efficiency is possible over the tested genomic DNA (gDNA) concentration range, when the molecular weight of the PEI in the PEI/mPpy NWs is 25 kDa. In contrast, in the case of the PEI/mPpy NWs with low-molecular-weight PEI (800 Da), the efficiency significantly decreased with an increase in gDNA concentration. Therefore, when introduced onto nanowires, the PEI with a higher molecular weight (25 kDa) is found to exhibit higher binding and condensation capabilities as compared to the PEI with a lower molecular weight (800 Da). Such results signify that the formation of a DNA-PEI/mPpy NW complex through an electrostatic interaction is dependent on the molecular weight of PEI.

Figure 7C:
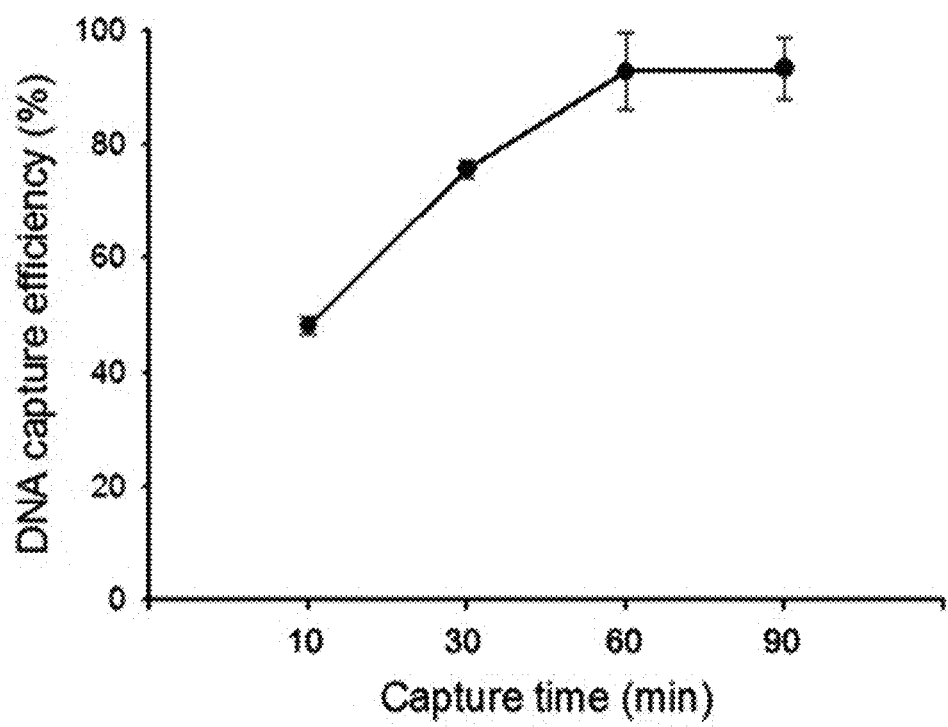
FIGS. 7C and 7D show a cfDNA recovery efficiency of the PEI/mPpy NWs according to the present invention when genomic DNA obtained from HPV18-positive (HeLa) cells or HPV16-positive (SiHa) cells was ex vivo spiked into the HPV-negative urine pool and allowed to react for various reaction times.
Figure 7D:
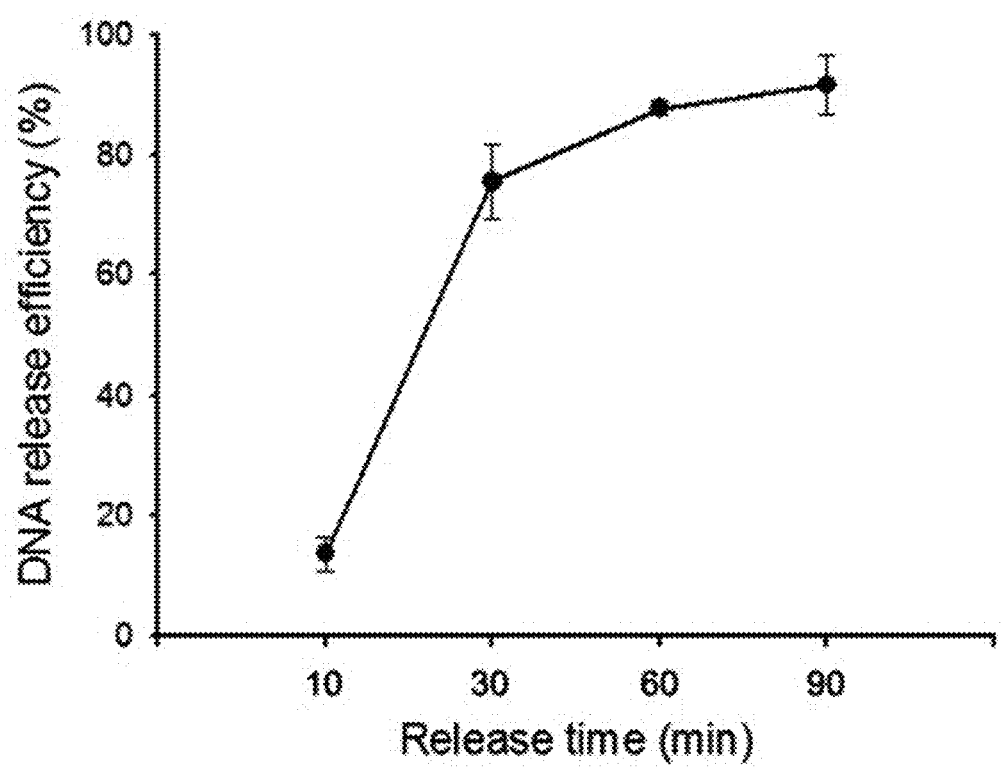

Also, when the genomic DNA obtained from HPV18-positive (HeLa) cells or HPV16-positive (SiHa) cells was mixed with an HPV-negative urine sample and were allowed to react for varying durations, the DNA capture efficiency and DNA recover (release) efficiency were found to be higher with a longer reaction time, as shown in FIGS. 7C and 7D. More specifically, the DNA capture efficiency and DNA recover (release) efficiency improved when the molecular weight of PEI in the PEI/mPpy NWs was 25 kDa and the reaction time was 60 minutes or longer. Based on the results, conditions under which the DNA recover (release) efficiency and stability are improved can be identified.

3-2. Determination of DNA Detection Limit (LOD) of PEI/mPpy NWs in Urine Samples To determine the DNA detection limit of the PEI/mPpy NWs in urine samples, a known amount of the genomic DNA obtained from a HeLa cell line (contains HPV18 at a ratio of 10 to 50 copies/cell) or a SiHa cell line (contains HPV16 at a ratio of 1 to 2 copies/cell) was spiked ex vivo with individual HPV-negative urine samples. Then, 0.5 mg/ml PEI/mPpy NWs were added into each sample, the mixture was subjected to shaking at 1,000 rpm for one hour at room temperature, and HPV DNA was eluted with nuclease-free water. Finally, the DNA thus recovered was mixed with an equal amount of a cobas HPV master mix, and was amplified with Roche LC480.

As shown in FIG. 8, when a known amount of the genomic DNA obtained from a HeLa cell line (contains HPV18 at a ratio of 10 to 50 copies/cell) or a SiHa cell line (contains HPV16 at a ratio of 1 to 2 copies/cell) was spiked ex vivo with the HPV-negative urine sample, the LOD was found to be different for each HPV genotype. The LOD of PEI/mPpy NW in urine samples was found to be 10 cells/ml for HPV16 and 30 cells/ml for HPV18.

3-3. HPV DNA Isolation by PEI/mPpy NW in Urine Samples

By using 0.5 mg/ml PEI/mPpy NWs and a QIAamp Circulating Nucleic Acid Kit (Qiagen Kit®; Qiagen), cfDNA was extracted from HPV-positive and HPV-negative urine samples (300 µl each) in accordance with the manufacturer's instruction. The yield of cfDNA eluted from urine was determined through PicoGreen fluorescence analysis and gel electrophoresis analysis for direct quantification and visualization. Subsequently, for the detection and genotyping of 13 µl of the eluted DNA, the DNA was mixed with an equal volume of a cobas HPV master mix reagent, and the target HPV DNA was amplified with the Roche cobas 4800 HPV Test. The analytical efficiency and clinical efficiency of the PEI/mPpy NWs according to the present invention was assessed by detecting urine-based HPV DNA. The analysis was conducted on urine samples or cervical swab specimens from total of 27 HPV-positive patients.

Figure 9A:
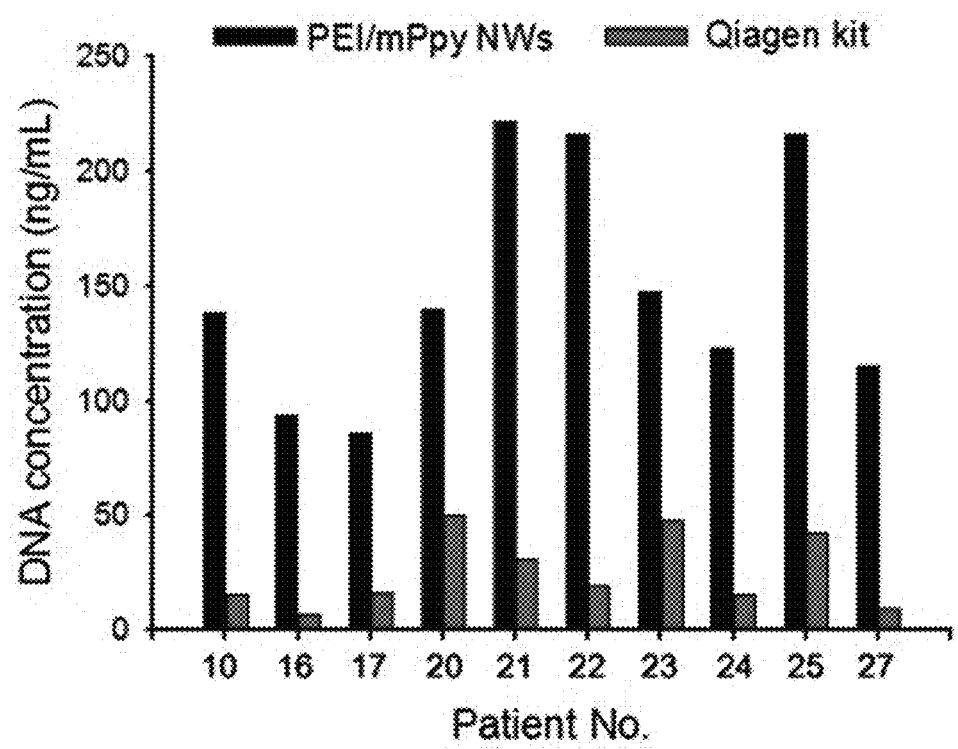
FIG. 9A shows the concentration of cfDNA recovered from urine samples obtained from cervical cancer patients.

As shown in FIG. 9A, when the concentration of the cfDNA extracted from urine samples of ten cervical cancer patients by using the PEI/mPpy NWs (black bars) or a Qiagen Kit® (red bars) was measured, it was found that the total amount of cfDNA obtained from urine samples by using the PEI/mPpy NWs was as much as about four times greater than the amount obtained using the Qiagen Kit®. More specifically, when HPV DNA was efficiently extracted from urine samples using the PEI/mPpy NWs or the Qiagen Kit® and a genotype profile was identified, the HPV extracted with the PEI/mPpy NWs was found in 26 (96%) out of 27 HPV-positive specimens, whereas the HPV DNA extracted with the Qiagen kit (was detected in 16 (59%) specimens. Also, the HPV DNA extracted with the PEI/mPpy NWs had a much lower Ct value as compared to the HPV DNA extracted with the Qiagen Kit®. Such results strongly suggest the high performance of the PEI/mPpy NWs according to the present invention in terms of DNA recovery yield and integrity.

Also, as shown in FIG. 9B, the eluted cfDNA was found to be closely related to HPV DNA genotyping. The HPV genotype profiling of cervical cancer patients was performed using cervical swab specimens, and the genotype profile was identified by conducting the Roche cobas 4800 HPV Test on high-risk HPV types (HPV16, HPV18, and 12 other types). More specifically, when the PEI/mPpy NWs were used, it was found that the DNA extracted from urine samples had a similar HPV genotype distribution to the DNA extracted from cervical swab specimens.

The results show that, by having a long form, the PEI/mPpy NWs according to the present invention may have many interactions with HPV DNA while maintaining bioactivity, the duration and frequency of exposure increases, and thus the overall yield of the target HPV sequence is significantly improved. By having a large surface-to-volume ratio and being capable of freely moving through the complex constituents present in urine, pencil-shaped PEI/mPpy NWs may preferentially bind to the HPV DNA.

3-4. Evaluation of HPV Genotype Distribution Pattern in Urine Samples of Cancer Patients or Healthy Control Group Obtained Using PEI/mPpy NWs To evaluate the clinical performance of urine-based HPV detection, HPV genotype distribution patterns were obtained from urine samples of cancer patients or a healthy control group and were compared to the patterns obtained from cervical swab specimens. A total of 35 urine samples (30 HPV-positive and five HPV-negative samples) obtained from cervical cancer patients and a healthy control group were mutually compared in terms of the amount of the cfDNA extracted therefrom by using the PEI/mPpy NWs.

Figure 10A:
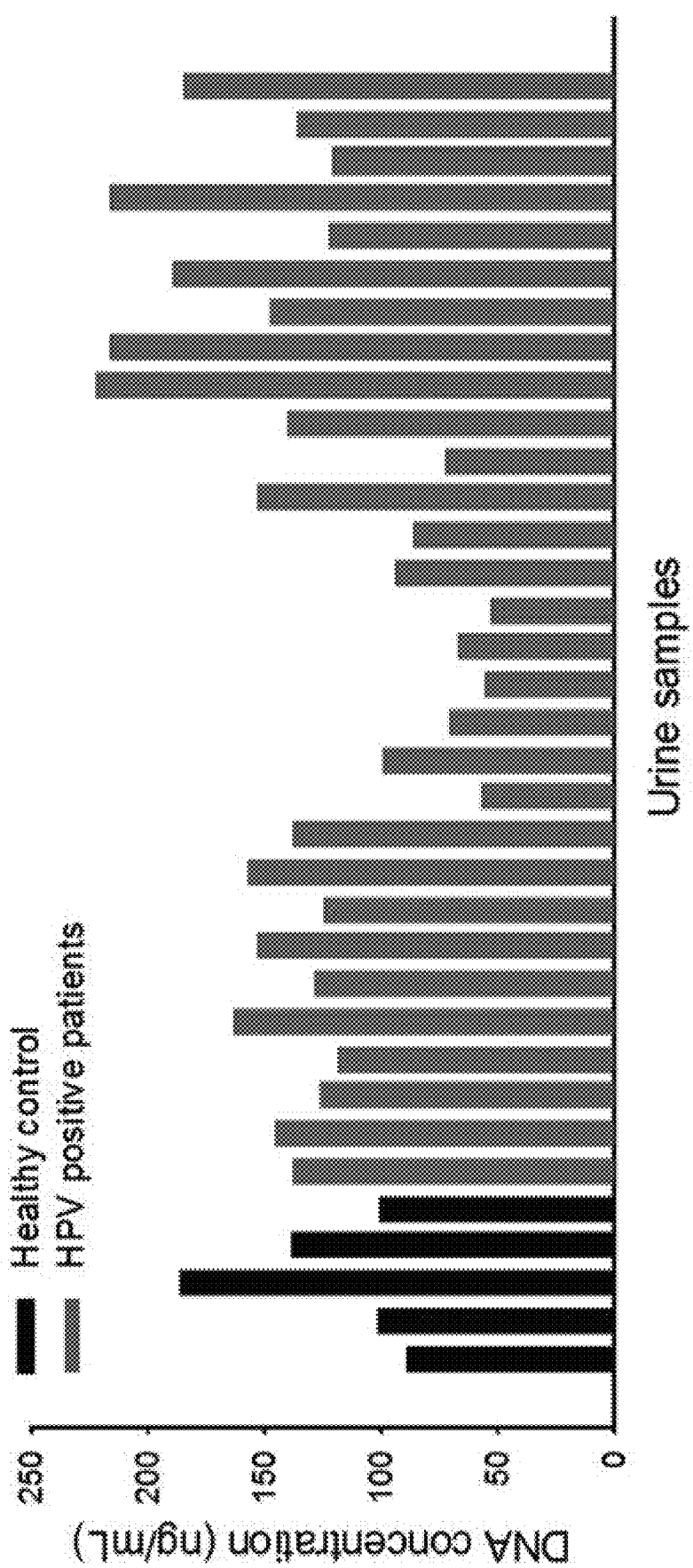
FIG. 10A shows the measured concentration of cfDNA isolated from urine samples of cervical cancer patients and a healthy control group by using the PEI/mPpy NWs according to the present invention.

Results as shown in FIG. 10A confirm that there is no significant difference in the concentration of the cfDNA extracted with the PEI/mPpy NWs from the cervical cancer patients and the healthy control group.

Figure 10B:
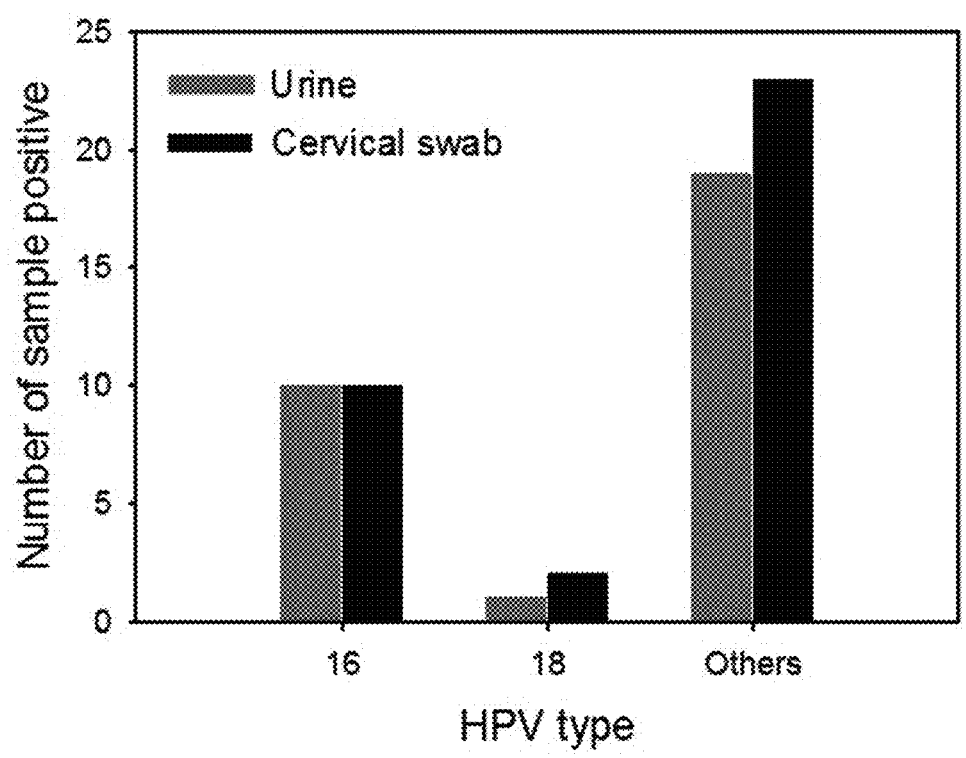

Also, as shown in FIGS. 10B and 10C, when type-specific HPV detection was further investigated using a pair of samples consisting of a cervical swab specimen and a 300 μl urine sample, the HPV-type detection results obtained respectively from the urine sample and the cervical swab specimen were highly consistent with each other by as much as 83%, even though the amount of urine sample was as little as 300 μl. Such results suggest that the use of the PEI/mPpy NWs in urine-based HPV screening is highly advantageous for the extraction, identification, and analysis of various high-risk HPV DNA genotypes.

Circulating cfDNA was extracted from a urine sample of a cervical cancer patient to successfully evaluate the performance of the PEI/mPpy NWs according to the present invention, and then HPV DNA by type was identified and detected to prove the clinical utility of the PEI/mPpy NWs. In the development and evaluation of clinical screening and diagnosis of cervical cancer as a part of a large-scale clinical trial, an HPV DNA isolation and detection strategy based on the PEI/mPpy NWs is considered to be a cost-effective and widely applicable technique due to higher sensitivity and accuracy thereof as compared to other urine-based methods.

Example 4. Efficiency Assessment of PEI/mPpy NWs in Blood Plasma or Cerebrospinal Fluid (CSF) Samples 4-1. Assessment of DNA Detection Efficiency of PEI/mPpy NWs The PEI/mPpy NWs were prepared according to Example 1 to effectively detect cfDNA in blood plasma. Low-range (10 to 100 bp), middle-range (100 to 2000 bp), or high-range (3.5 to 21 kb) DNA ladders with a varying concentration were spiked with healthy human blood plasma.

Figure 11A:
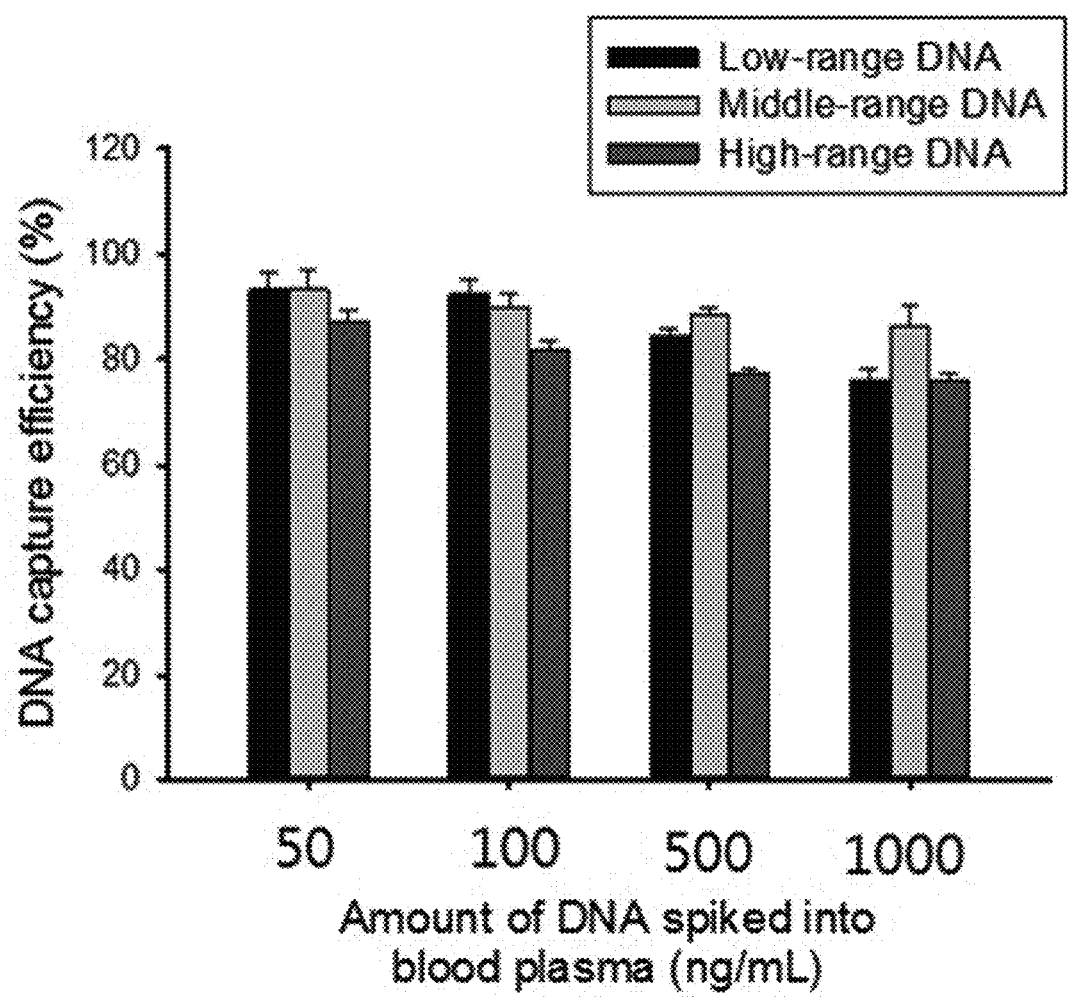
FIG. 11A shows a cfDNA capture efficiency by DNA size of the PEI/mPpy NWs according to the present invention.

As shown in FIG. 11A, when the detection efficiency by size of the cfDNA extracted with the PEI/mPpy NWs according to the present invention was assessed, it was found that high-efficiency tumor-derived cfDNA extraction from small fragments circulating within blood plasma is possible irrespective of DNA concentration.

4-2. Assessment of DNA Capture Efficiency as Function of PEI/mPpy NW Length

To assess DNA detection efficiency as a function of the PEI/mPpy NW length, PEI/mPpy NWs with a varying length (in forms of magnetic nanoparticles, and PEI/mPpy NWs with a length of 7 μm and 16 μm) were prepared.

Figure 11B:
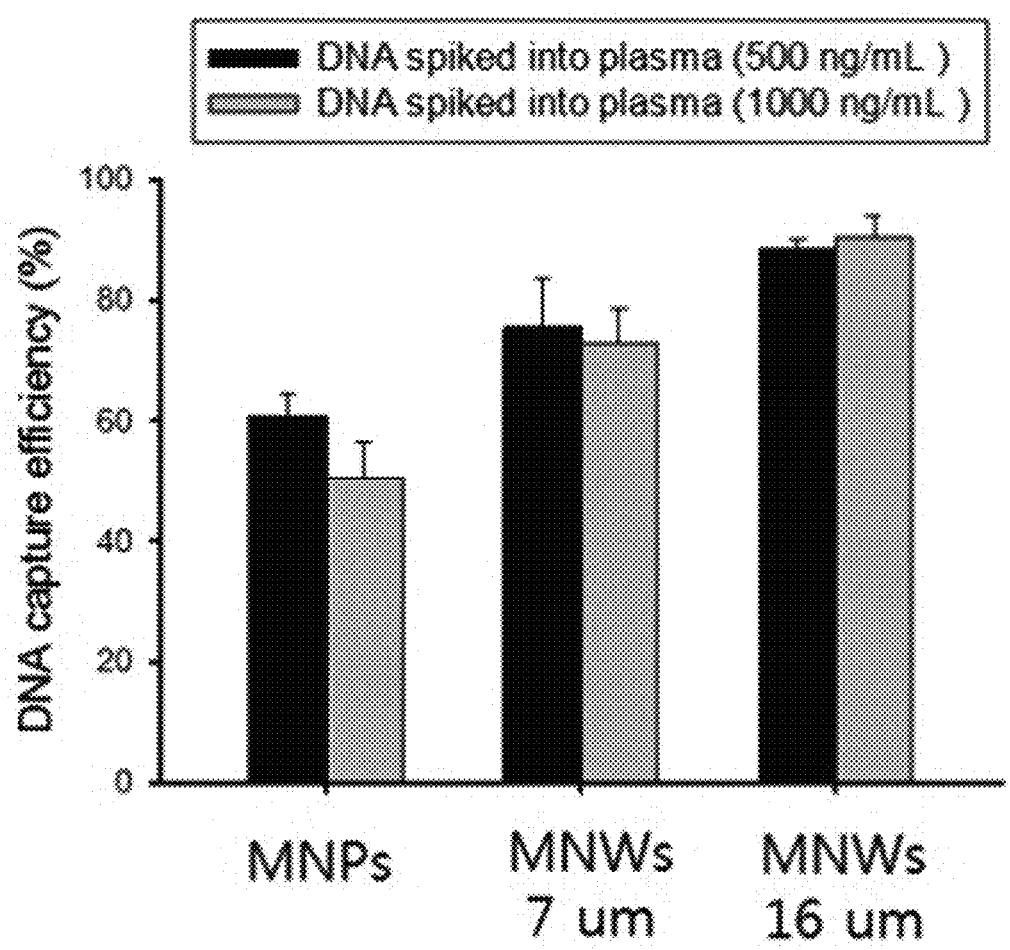
FIG. 11B shows a DNA capture efficiency by magnetic nanostructure length of the PEI/mPpy NWs according to the present invention.

Results as shown in FIG. 11B confirm that longer PEI/mPpy NWs are more advantageous for tumor-derived cfDNA extraction from small fragments circulating within blood plasma.

4-3. Comparison of DNA Detection Efficiency of PEI/mPpy NWs and Qiagen Kit®

To compare the PEI/mPpy NWs and the Qiagen Kit®, which is the most commonly used product, in terms of DNA detection efficiency, cfDNA capture/extraction efficiency from blood plasma was compared. Low-range (10 to 100 bp), middle-range (100 to 2000 bp), or high-range (3.5 to 21 kb) DNA ladders were spiked with healthy human blood plasma. Also, cfDNA detection efficiency by size was analyzed through gel electrophoresis.

Figure 11C:
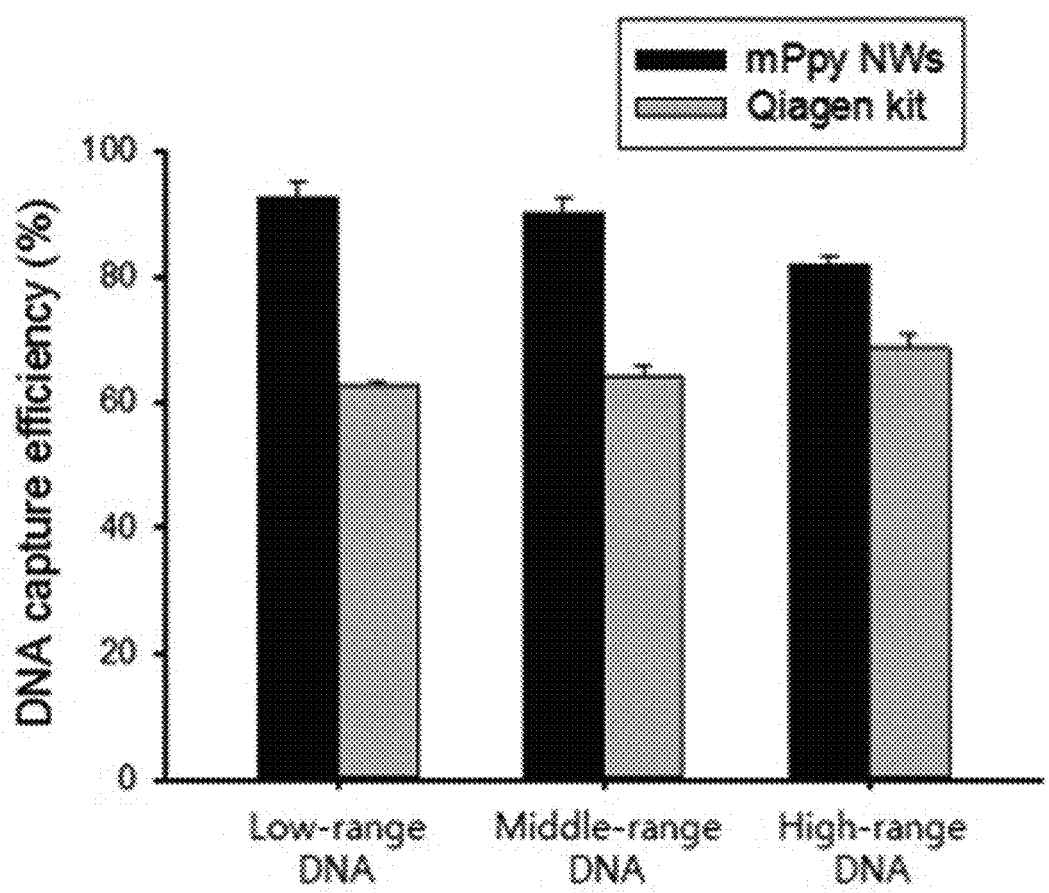
FIG. 11C compares the PEI/mPpy NWs according to the present invention and a commercial Qiagen Kit® in terms of DNA capture efficiency.
Figure 11D:
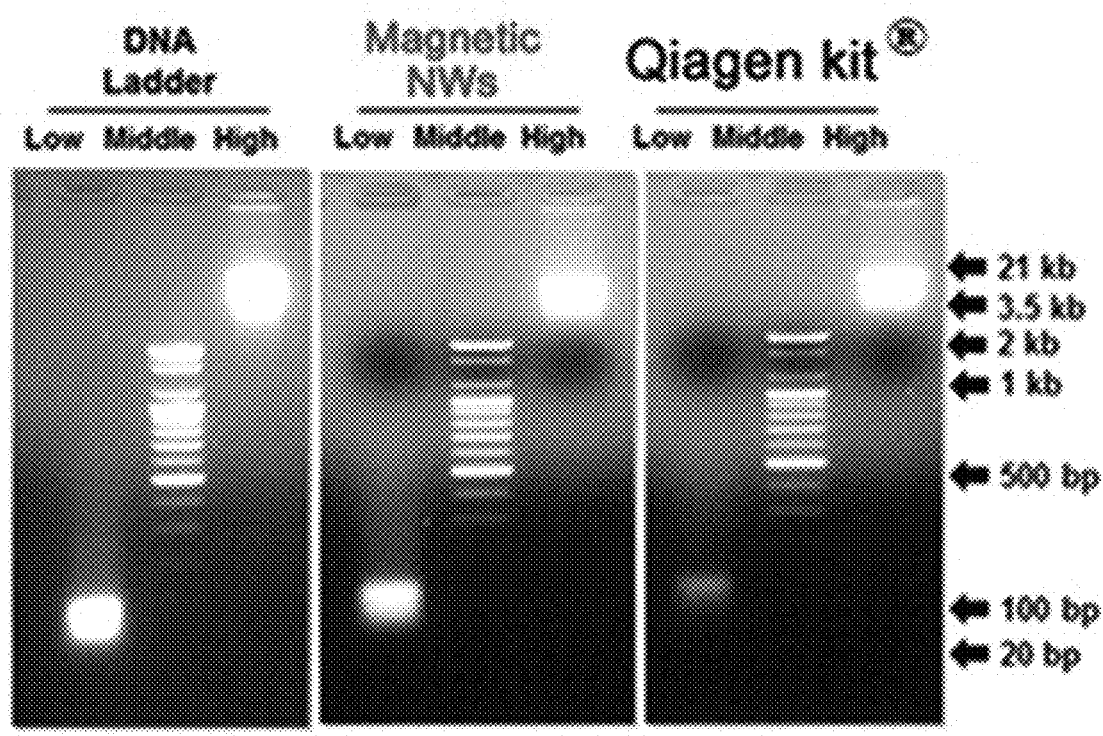
FIG. 11D compares the PEI/mPpy NWs according to the present invention and the commercial Qiagen Kit® in terms of DNA recovery efficiency.

Results as shown in FIG. 11C confirm that the cfDNA detection efficiency of the PEI/mPpy NWs according to the present invention is significantly higher as compared to commercial products. Also, results as shown in FIG. 11D illustrate that the PEI/mPpy NWs according to the present invention exhibit a significantly higher recovery efficiency compared to the Qiagen Kit®, and accordingly, it is expected that the PEI/mPpy NWs according to the present invention will be highly advantageous for tumor-derived cfDNA extraction from small fragments circulating within blood plasma.

4-4. Comparison of DNA Detection Efficiency of PEI/mPpy NWs and Qiagen Kit® in Blood Plasma Samples of Breast Cancer or Lung Cancer Patients To evaluate a cfDNA detection capability of the PEI/mPpy NWs according to the present invention, the PEI/mPpy NWs were compared to the Qiagen kite in terms of DNA detection efficiency in blood plasma samples of breast cancer or lung cancer patients.

Figure 11E:
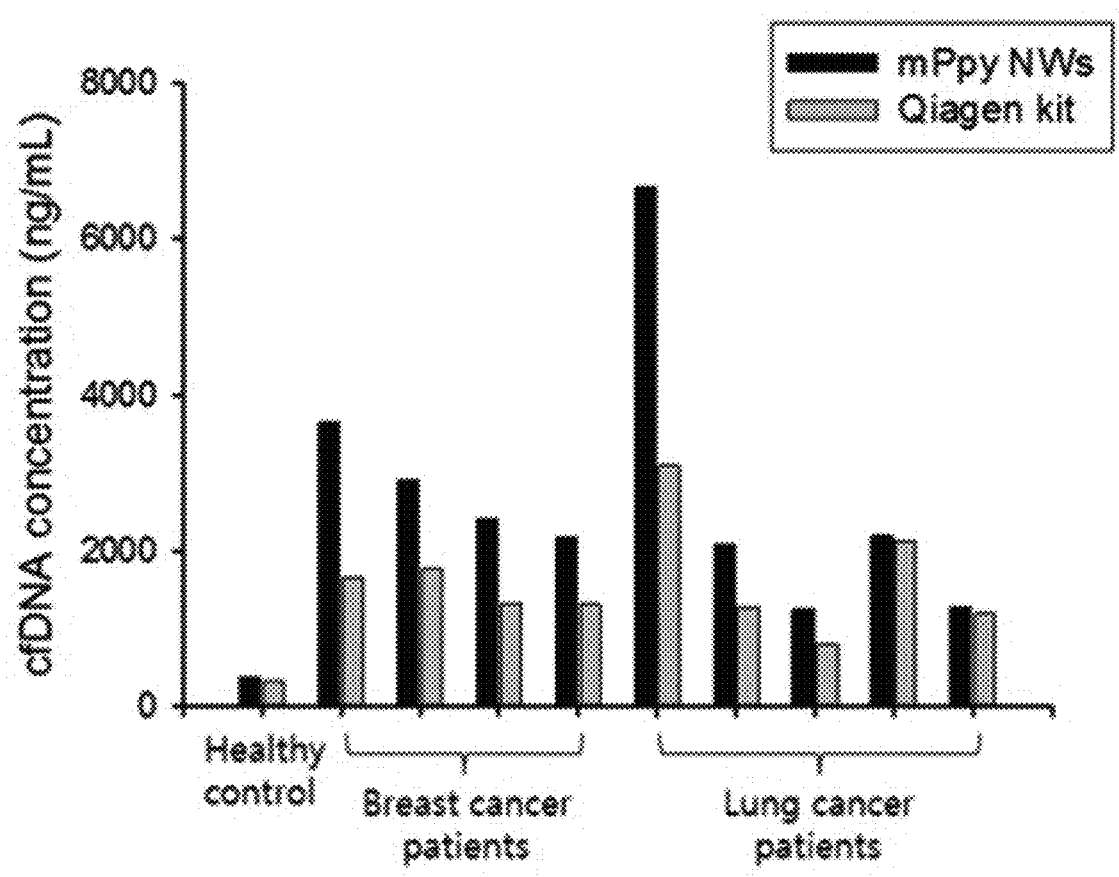
FIG. 11E compares the PEI/mPpy NWs according to the present invention and the commercial Qiagen Kit® in terms of cfDNA detection efficiency from blood plasma of breast cancer patients and lung cancer patients.

Results as shown in FIG. 11E confirm that the PEI/mPpy NWs according to the present invention exhibit a significantly higher cfDNA detection efficiency as compared to commercial products in most patient groups.

4-5. Identification of Mutation in DNA Extracted with PEI/mPpy NWs and Qiagen Kit® from Blood Plasma Samples of Lung Cancer Patients To identify mutations in DNA extracted with the PEI/mPpy NWs and the Qiagen kite from blood plasma samples of lung cancer patients, any detected cfDNA mutation was identified using droplet digital PCR (ddPCR).

As shown in FIG. 11F, since most cancer-related cfDNA fragments circulating within blood plasma have a size of 200 bp or less, the tumor-related cfDNA extraction efficacy of PEI/mPpy NWs is superior to that of a commercial kit, and mutation results consistent with cancer tissue results were obtained.

In particular, when cfDNA was extracted from the blood plasma of ten lung cancer patients by the use of the PEI/mPpy NWs according to the present invention or the Qiagen Kit®, and then ddPCR was performed thereon, mutation results consistent with cancer tissue results were obtained from the blood plasma of five patients with EGFR exon 21 L858R mutation for both the PEI/mPpy NWs and the Qiagen Kit®.

Also, a mutation was observed when the PEI/mPpy NWs were used with patient's blood plasma as little as 300 μl, just as when the Qiagen kite was used with 1 ml of patient's blood plasma. In particular, when the PEI/mPpy NWs according to the present invention were used, the amount of wild-type DNA was found to be relatively much lower than the amount of mutant DNA. Therefore, it is expected that the PEI/mPpy NWs according to the present invention will be highly advantageous for tumor-derived cfDNA extraction from small fragments circulating within blood plasma.

In addition, cfDNA was extracted from the blood plasma of the group of the remaining five lung cancer patients, i.e., the patients with EGFR exon 19 E746_A750del mutation, in the same manner by using the PEI/mPpy NWs according to the present invention or the Qiagen Kit®. When the cfDNA detected with the PEI/mPpy NWs was examined through ddPCR, mutation results consistent with cancer tissue results were obtained from four out of the five patients. However, in the case of the Qiagen Kit®, no mutation was found in any of the five patients. Even with a small amount (i.e., 300 μl) of blood plasma, the PEI/mPpy NWs exhibited a cfDNA detection efficiency that is consistent with cancer tissue results.

Figure 11G:
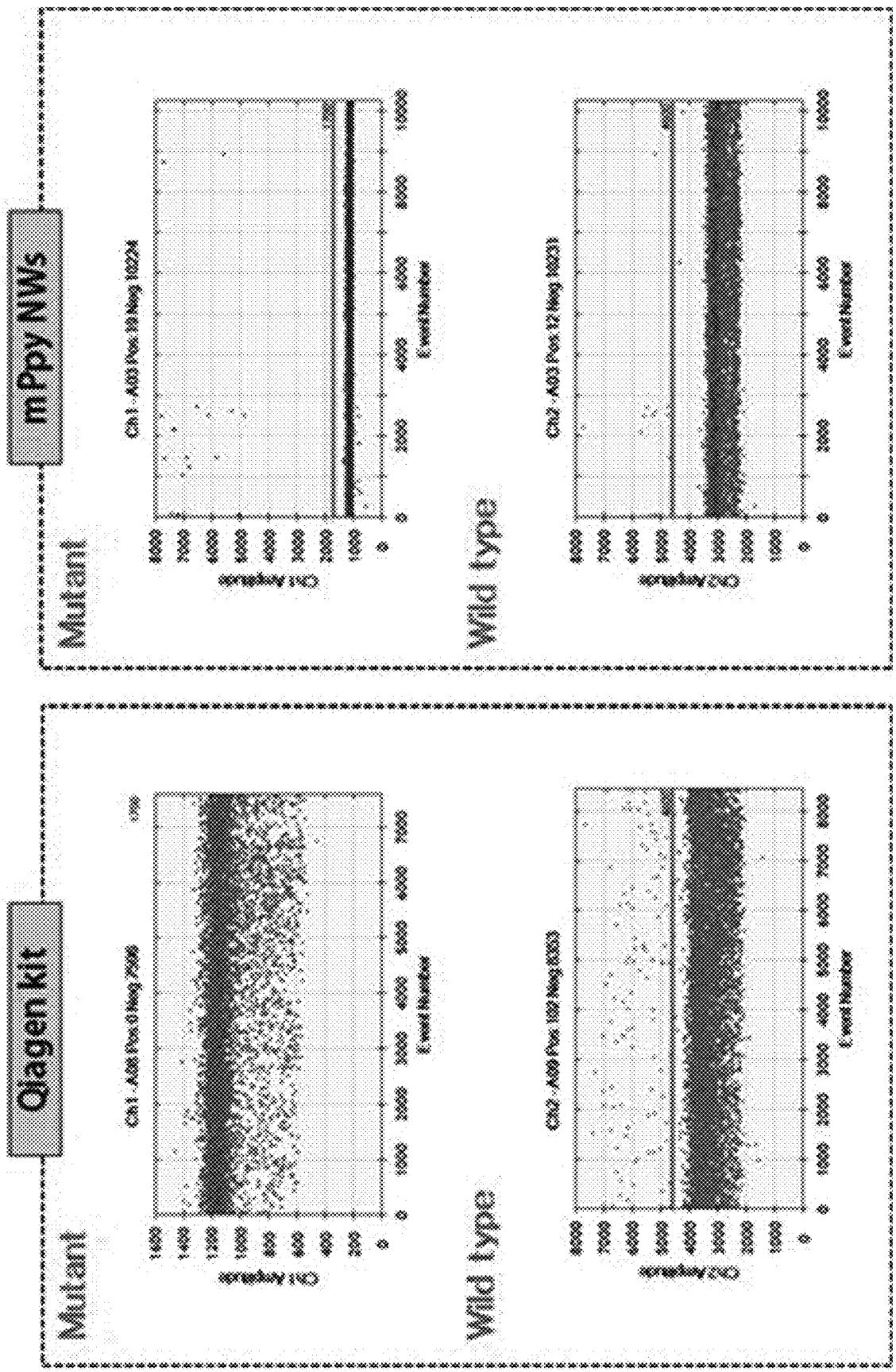
FIG. 11G shows EGFR exon 19 E746_A750del mutation examined after DNA extraction with the PEI/mPpy NWs according to the present invention and the commercial Qiagen Kit®.

Also, cfDNA was extracted from the blood plasma of lung cancer patients by using the PEI/mPpy NWs or the Qiagen Kit®, ddPCR was performed thereon, and the cfDNA detected from the blood plasma of the lung cancer patients with EGFR exon 19 E746_A750del mutation was amplified. According to the results as shown in FIG. 11G, a large amount of wild-type DNA and no mutant DNA were identified in the cfDNA detected with the Qiagen Kit®. In contrast, when the PEI/mPpy NWs were used for cfDNA detection from patient's blood plasma, not a large amount of wild-type DNA was identified from the cfDNA, but mutant DNA was clearly visible.

Figure 11H:
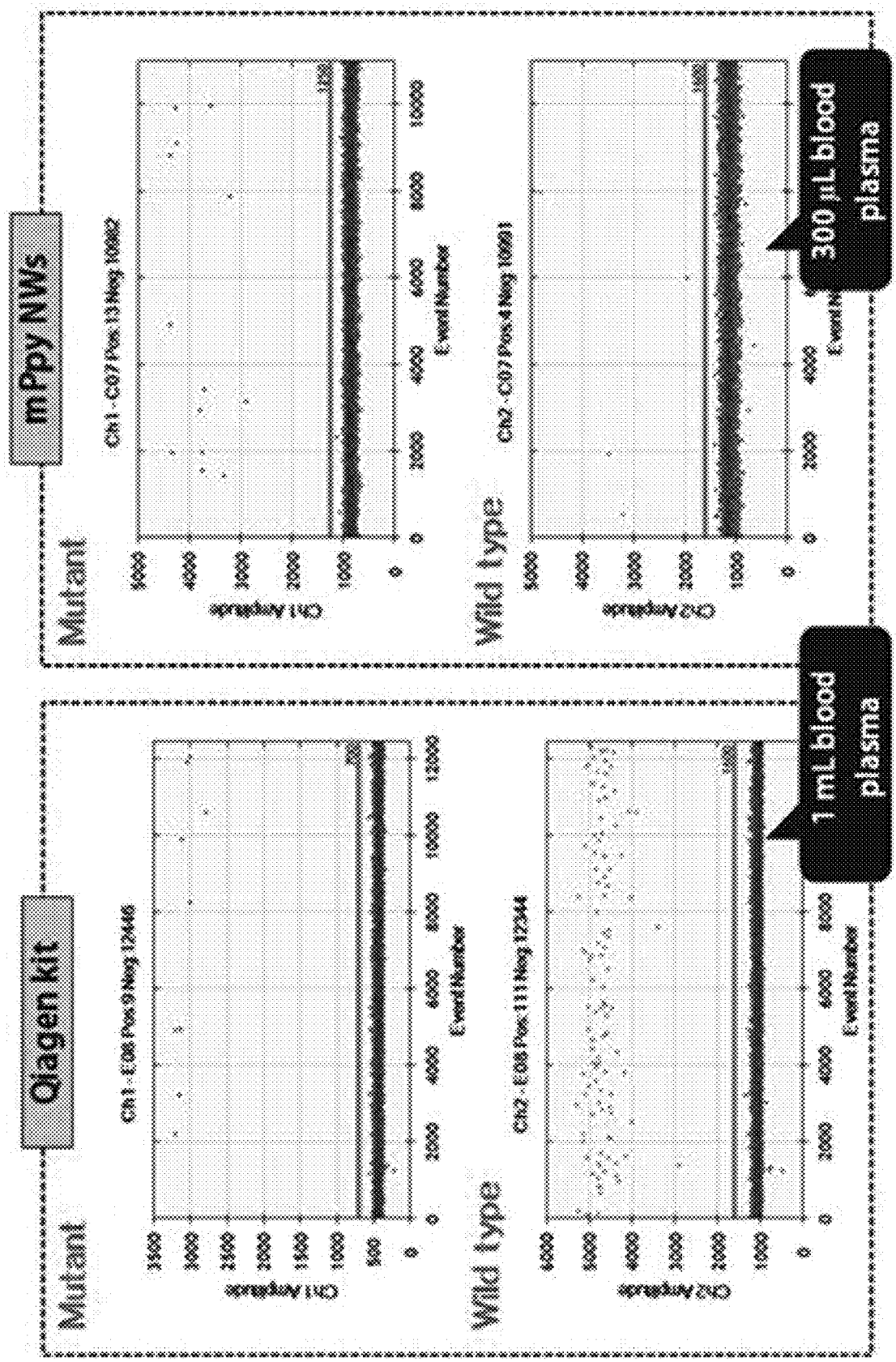
FIG. 11H shows EGFR exon 21 L858R mutation examined after DNA extraction with the PEI/mPpy NWs according to the present invention and the commercial Qiagen Kit®.

Also, when cfDNA was extracted from the blood plasma of lung cancer patients by using the PEI/mPpy NWs or the Qiagen Kit®, ddPCR was performed thereon, and the cfDNA detected from the blood plasma of the lung cancer patients with EGFR exon 21 L858R mutation was amplified. According to the results as shown in FIG. 11H, a large amount of wild-type DNA is present in the cfDNA detected with the Qiagen Kit®. In contrast, when the PEI/mPpy NWs were used for cfDNA detection, not a large amount of wild-type DNA and mutant DNA at a level similar to the case of the Qiagen kite were identified from the cfDNA. While the PEI/mPpy NWs extracted cfDNA from 300 μl of blood plasma, the amount of the blood plasma used with the Qiagen Kit® was 1 ml.

4-6. Efficiency Assessment of PEI/mPpy NWs in CSF Samples

To examine the mutation of the DNA extracted from blood plasma samples or CSF samples of lung cancer patients according to the method of Example 4-5, the mutation of the detected cfDNA was identified through ddPCR.

As shown in FIG. 11I, when the mutation of the cfDNA detected from the blood plasma or CSF of lung cancer patients by using the PEI/mPpy NWs according to the present invention was compared to the gene mutation of cancer tissues, the results from the cfDNA detected from the body fluid of nine patients were consistent with the cancer tissue results.

The above description of the present invention is for purposes of illustration, and it will be understood by those with ordinary skill in the technical field, to which the present invention belongs, that variations to other specific forms are possible without changing the technical spirit or essential features of the present invention. Therefore, it should be understood that the examples described above are intended to be illustrative and as non-limiting in all aspects.

What is claimed is:

1. A magnetic nanowire for detecting and isolating cell-free DNA (cfDNA),
   wherein the magnetic nanowire comprises polypyrrole in which iron oxide nanoparticles and biotin are incorporated,
   the magnetic nanowire is surface-treated with polyethyleneimine containing biotin, wherein the polyethyleneimine is conjugated onto the surface of the magnetic nanowire via a biotin-streptavidin-biotin interaction, and
   the magnetic nanowire is prepared by electrochemical deposition.

2. A cancer diagnosis kit comprising the magnetic nanowire according to claim 1.

3. A method of detecting and isolating cell free DNA (cfDNA), the method comprising:
   (1) treating a sample with a magnetic nanowire,
   wherein the magnetic nanowire comprises polypyrrole in which iron oxide nanoparticles and biotin are incorporated,
   the magnetic nanowire is surface-treated with polyethyleneimine containing biotin, wherein the polyethyleneimine is conjugated onto the surface of the magnetic nanowire via a biotin-streptavidin-biotin interaction, and
   the magnetic nanowire is prepared by electrochemical deposition;
   (2) inducing attachment of the cfDNA included in the sample to the magnetic nanowire;
   (3) isolating, from the sample, the magnetic nanowire to which the cfDNA is attached; and
   (4) separating, by changing pH, the cfDNA from the isolated magnetic nanowire.

4. The method according to claim 3, wherein the sample is urine, cerebrospinal fluid (CSF), blood plasma, or blood.

5. A method of diagnosing cancer, comprising the method of claim 3; and
   analyzing the cfDNA.

6. A method of providing information for diagnosing the onset and/or prognosis of cancer, comprising the method of claim 3; and analyzing the cfDNA.

7. The method of claim 6, wherein the analysis of the cfDNA confirms the presence of a gene mutation by analyzing a concentration, number of copies, or base sequence of DNA in a sample.

* * * * *